United States Patent [19]
Carver et al.

[11] Patent Number: 5,773,239
[45] Date of Patent: Jun. 30, 1998

[54] MANNOSIDASE INHIBITORS, PROCESS FOR THEIR PREPARATION AND THEIR USE AS THERAPEUTIC AGENTS

[75] Inventors: Jeremy Carver, Toronto; James Wilson Dennis, Etobicoke; Rajan Shah, Toronto, all of Canada

[73] Assignees: Mount Sinai Hospital Corporation.; GlycoDesign, Inc., both of Toronto, Canada

[21] Appl. No.: 568,127

[22] Filed: Dec. 6, 1995

Related U.S. Application Data

[63] Continuation-in-part of Ser. No. 346,278, Nov. 22, 1994, abandoned, which is a continuation-in-part of Ser. No. 137,797, Oct. 19, 1993, abandoned.

[51] Int. Cl.[6] .............................. C12Q 1/02; C12Q 1/48; C12Q 1/34; C12Q 1/00
[52] U.S. Cl. .............................. 435/29; 435/15; 435/18; 435/13; 435/4; 435/19; 548/530
[58] Field of Search .................. 435/29, 15, 18, 435/13, 4, 19; 548/530

[56] References Cited

U.S. PATENT DOCUMENTS

| | | | |
|---|---|---|---|
| 4,457,919 | 7/1984 | Simon et al. | 424/180 |
| 4,837,237 | 6/1989 | Rohrschneider et al. | 514/62 |
| 4,839,290 | 6/1989 | Kaieda et al. | 435/240.23 |
| 4,996,329 | 2/1991 | Fleet et al. | 548/543 |
| 5,075,448 | 12/1991 | Fleet | 546/112 |
| 5,075,457 | 12/1991 | Fleet | 548/543 |
| 5,109,116 | 4/1992 | Arkwright et al. | 530/395 |
| 5,206,356 | 4/1993 | Pierce et al. | 536/53 |
| 5,240,707 | 8/1993 | Farr et al. | 424/405 |
| 5,262,425 | 11/1993 | Farr et al. | 514/299 |

FOREIGN PATENT DOCUMENTS

| | | |
|---|---|---|
| 2040058 | 4/1990 | Canada . |
| 0193770 | 9/1986 | European Pat. Off. . |
| PCT/US92/ 06707 | 4/1993 | WIPO . |

OTHER PUBLICATIONS

Fuhrmann, E., et al., Nature, 307:755, 1984.
Colegate et al., Aust. J. Chem. 32:2257–2264, 1979.
Molyneux R.J and James L.F., Science 215:190–191, 1981.

(List continued on next page.)

*Primary Examiner*—Louise Leary
*Attorney, Agent, or Firm*—Merchant, Gould, Smith Edell, Welter & Schmidt

[57] ABSTRACT

The invention relates to novel mannosidase inhibitors, processes for their preparation and their use as therapeutic agents. The invention also relates to the use of compounds of the formula II as described herein as prodrugs.

31 Claims, 8 Drawing Sheets

OTHER PUBLICATIONS

Schneider et al., Tetrahedron 39:29–32, 1983.
Tulsiani et al., J. Biol. Chem, 257:7936–7939, 1982.
Fernandes et al., Cancer Res. 51:718–723, 1991.
Dennis J.W., Cell Surface Carbohydrates and Cell Dev., pp. 161–0194. CRC Press, Boca Raton, 1991.
Dennis et al., Science 236:582–585, 1987.
VanderElst I. and Dennis J.W., Exp. Cell Res. 192:612–621, 1991.
Dennis J.W., Cancer Res. 46:5131–5136, 1986.
Humphries et al., Proc. Natl. Acad. Sci. U.S.A. 83:1752–1756, 1986.
Yagel et al., Int. J. Cancer 44:685–690, 1989.
Seftor et al., Melanoma Res. 1:43–54, 1991.
Dennis et al., J. Natl. Cancer Inst. 81:1028–1033, 1989.
Dennis et al., Cancer Res. 50:1867–1872, 1990.
Humphries M.J. and Olden K., Pharmacol Ther. 44:85–105, 1989.
Olden et al., Pharmacol Ther. 50:285–290, 1991.
Humphries et al., Cancer Res. 48:1410–1415, 1988.
Yagita M. and Saksela E., Scand. J. Immunol. 31:275–282, 1990.
White et al., Biochem. Biophys. Res. Commun. 150:615–625, 1988.
Bowlin et al., Cancer Res. 49:4109–41113, 1989.
White et al., Cancer Commun. 3:83–91, 1991.
Oredipe et al., J. Natl. Cancer Institue 83:1149–1156, 1991.
Fleet G.W.J. et al., Chem. Soc. Commun., 1984, 1240–1241.
Palamarczyk et al., Arch. Biochem. Biophys. 243:35–45, 1985.
Fleet et. al., FEBS Lett. 237:128–132, 1988.
Fleet et al., Tetrahedron 44:2649–2655, 1988. (Abstract).
Hino et al., J. Antibiotics, 38(7):926–935, 1985.

MANNOSIDASE INHIBITORS, PROCESS FOR THEIR PREPARATION AND THEIR USE AS THERAPEUTIC AGENTS

This application is a continuation-in-part of U.S. Ser. No. 08/346.278 filed Nov. 22, 1994, now abandoned, which is a continuation-in-part of U.S. Ser. No. 08/137,797 filed Oct. 19, 1993 now abandoned.

FIELD OF THE INVENTION

The present invention relates generally to novel mannosidase inhibitors, processes for their preparation and their use as therapeutic agents.

BACKGROUND OF THE INVENTION

Swainsonine, 1,5-dideoxy-1,5-imino-5-mannitol and 1,4-dideoxy-1,4-imino-D-mannitol are mannosidase inhibitors. Each of the compounds inhibits a different mannosidase of glycoprotein processing (Fuhrmann, E. et al., Nature, 1984, 307:755).

Swainsonine (SW) is an indolizidine alkaloid found in Australian *Swainsona canescens* (Colegate et al., Aust J Chem 32:2257–2264, 1979), North American plants of the genera *Astragalus* and Oxytropis (Molyneux R. J. and James L. F., Science 215:190–191, 1981), and also the fungus *Rhizoctonia leguminicola* (Schneider et al., Tetrahedron 39;29–31, 1983). The alkaloid is a potent inhibitor of the Golgi enzyme α-mannosidase II, an enzyme required for maturation of N-linked oligosaccharides on newly synthesized glycoproteins. SW also blocks lysosomal α-mannosidases causing the accumulation of oligomannose chains in cells exposed to the drug (Tulsiani et al., J. Biol. Chem. 257:7936–7939, 1982). The SW-block in Golgi processing prevents expression of the β1–6GlcNAc branched "complex-type" N-linked oligosaccharides which has been observed to increase following malignant transformation in human and rodent cells (Fernandes et al., Cancer Res. 51:718–723, 1991 and Dennis, J. W., pp. 161–194. CRC Press, Boca Raton, 1991). The branched oligosaccharides appear to play a role in cancer metastasis, as loss or truncation of the structures due to somatic mutations in metastatic tumor cell lines results in greatly reduced metastasis and slower solid tumor growth (Dennis et al., Science 236:582–585, 1987 and VanderElst I and Dennis J. W., Exp. Cell Res. 192:612–613, 1991). Furthermore, SIV-treated murine tumor cells are less metastatic in both organ-colonization and spontaneous metastasis assays in mice (Dennis J. W., Cancer Res. 46:5131–5136, 1986 and Humphries et al., Proc. Nati. Acad. Sci. USA 83:1732–1756, 1986). SW has been shown to block tumor cell invasion through extracellular matrix in vitro (Yegel et al., Int. J. Cancer 44:685–690, 1989 and Seftor et al., Melanoma Res. 1:53–54, 1991). SW administered either orally or by mini-osmotic pumps to athymic nude mice inhibited the growth rate of human MeWo melanoma and HT29m colon carcinoma tumor xenografts in the mice (Dennis et al., J. Natl. Cancer Inst. 81:1028–1033, 1989 and Dennis et al., Cancer Res., 50:1867–1872, 1990). The alkaloid has positive effects on cellular immunity in mice (reviewed in Humphries M.J. and Olden K. Pharmacol Ther. 44:85–105, 1989 and Olden et al., Pharmacol Ther 50:285–290, 1991)). In particular, SW has been shown to alleviate both chemically-induced and tumor-associated immune suppression (Hino et al., J. Antibiot. (Tokyo) 38:926935, 1985), increase NK cell (Humphries et al., Cancer Res. 48:1410–1415, 1988), LAK cell activities (Yagita M and Saksela E., Scand. J. Immunol. 31:27->282, 1990), and increase splenic and bone marrow (BM) cell proliferation (White et al., Biochem. Biophys. Res. Commun. 150;615–625, 1988; Bowlin et al. Cancer Res 49, 4109–4113, 1989 and White et al., Cancer Commun. 3:8391, 1991). The drug has also been shown to be hemorestorative in mice following treatment with both cycle-specific and nonspecific chemotherapeutic agents (Oredipe et al., J. Natl. Cancer Inst. 83:1149–1156, 1991). SW is being tested in phase I clinical trials of cancer patients, as a 5 day intravenous infusion. The preliminary results of this study suggest that the drug is well tolerated with this regime.

1,4-dideoxy-1,4-imino-D-mannitol is an azofuranose analogue of mannose. It is structurally related to swainsonine but lacks the ethano unit connecting the nitrogen to C-6. It has been shown to be a weak inhibitor of the hydrolysis of p-nitrophenyl α-D- and β-D-glucopyranosides by yeast a-glucosidase and almond emulsin βglucosidase. However, it has been shown to be a potent inhibitor of the hydrolysis of p-nitrophenol α-D-mannopyranoside by Jack Bean α-mannosidase (Canavalia ensiformis). (Fleet G.WJ., et al., J. Chem. Soc. Commun., 1984, 1240). It has also been reported to be an inhibitor of glycoprotein mannosidases (Palamarczyk et al., Arch. Biochem. Biophys. 35,243, 1985).

Derivatives of 1,4-dideoxy-1,4-imino-D-mannitol, 6-fluoro-1,4-imino-1,4,6-trideoxy-D-mannitol, and N-butyl and N-benzyl derivatives have been reported to have useful mannosidase inhibitory activity (U.S. Pat. No. 4,996,329). 1,4-dideoxy-1,4-imino-D-mannitol and it N-methyl derivatives have been tested as antiviral agents against human immunodeficiency viruses (Fleet et al., FEBS Lett. 237, 128, 1988).

Other inhibitors of mannosidase have been described in Canadian Published Patent Application No. 2,040,058, PCT/US92/06707 and EP-A 0193770. Canadian Published Patent Application No. 2,040,058 discloses mannosidase inhibitors which are substituted (1α, 2β, 3αa or β, 4a, 5a or β)-2,3,4-trihydroxy-5-(hydroxymethyl)-cyclopentylamines. PCT/US92/06707 discloses [4S-(4α,4aβ,5β,6α,7α,7aα)]-octahydro-1H-1-pyrindine-4,5,6,7-tetrols and [4R-(4α,4aα, 5α,6β,7β,7aβ)-octohydro-1H-1-pyrindine-4,5,6,7-tetrols, and EP-A 0193770 relates to derivatives of 3,4,5-trihydroxypiperidin.

SUMMARY OF THE INVENTION

The present inventors have surprisingly found that certain analogues of swainsonine and novel compounds developed by the inventors are ideally suited for use as prodrugs which are expected to have improved pharmacological properties and reduced side effects. The compounds are particularly useful as therapeutics in view of their enhanced membrane permeability properties.

The present invention therefore relates to a compound of the formula I

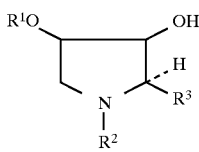

wherein
R$^1$ is hydrogen or p-nitrobenzoyloxy, -octanoyloxy or -butanoyloxy;

$R^2$ is hydrogen, $(C_1-C_5)$-alkyl, methyl cyclopropane, methyl cyclohexane, tertiary butyl or benzyl;

$R^3$ is —COOR$^4$ wherein $R^4$ is p-nitrobenzyl, octyl, or butyl;

—(CHOR$^1$)COOR$^4$ wherein $R^4$ is as defined above;

—CHR$^2$OR$^1$ wherein $R^1$ and $R^2$ are as defined above;

—(CHOR$^1$)(CHR$^2$OR$^1$) wherein $R^1$ and $R^2$ are as defined above;

—(CHOR$^1$)(CH$_2$R$^6$) wherein $R^1$ is as defined above and $R^6$ is a halogen preferably fluorine, chlorine, iodine or bromine; —CH$_2$R$^6$ wherein $R^6$ is as defined above; —CH$_2$O-CO—R$^4$ wherein $R^4$ is as defined above; or —CHR$^9$OH wherein $R^9$ is (C1–C5)-alkyl; with the proviso that when $R^1$ is hydrogen and $R^3$ is —(CHOH)(CH$_2$OH), $R^2$ cannot be methyl, n-butyl or benzyl and that when $R^1$ and $R^2$ are hydrogen, $R^3$ cannot be —CH$_2$OH, —(CHOH)CH$_3$, —(CHOH)(CH$_2$F) or —(CHOH)(CH$_2$OH).

The present invention also provides a process for the preparation of a compound of the formula I which comprises (i) N-alkylating 1,4-dideoxy-1,4-imino-2,3O-isopropylidene -α-D-lyxitol which is protected at the C5 position or 1,4-dideoxy-1,4-imino-2,3O-isopropylidene-α-D-mannitol which is protected at the C5 and C6 position, under suitable conditions with a compound of the formula R$^5$CHO wherein R$^5$ is $(C_1-C_5)$-alkyl, tertiary butyl or benzyl, cyclopropyl, and cyclohexyl, when a compound of the formula I is required wherein $R^2$ is $(C_1-C_5)$-alkyl, methyl cyclopropane, methyl cyclohexane, tertiary butyl or benzyl;

(ii) reacting 1,4-dideoxy-1,4-imino-2,3O-isopropylidene-α-D-lyxitol or 1,4-dideoxy-1,4-imino-2,3-O-isopropylidene-α-D-mannitol with a compound of the formula R$^6$—CO—R$^4$ wherein R$^6$ is a halogen preferably fluorine, chlorine, iodine, and bromine and R$^4$ is p-nitrobenzyl, octanyl or butyl under alkaline conditions, when a compound of the formula I is required wherein R$^3$ is CH$_2$O—CO—R$^4$ wherein R$^4$ is as defined above, or a compound of the formula I is required wherein R$^3$ is (CHOH)COOH;

(iii) reacting 1,4-dideoxy-1,4-imino-2,3-O-isopropylidene-α-D-lyxitol or 1,4-dideoxy-1,4-imino-2,3-O-isopropylidene-α-D-mannitol with triphenyl phosphine and C(R$^6$)$_4$ wherein R$^6$ is halogen preferably fluorine, chlorine, iodine or bromine, when a compound of the formula I is required wherein R$^3$ is CH$_2$R$^6$ wherein R$^6$ is as defined above or a compound of the formula I is required wherein R$^3$ is (CHOH)CH$_2$R$^6$; and esterifying the 6-deoxy-6-halo-mannitol derivative using the methods given where a compound of the formula I is required wherein R$^3$ is (CHOR$^1$)CH$_2$R$^6$;

(iv) preparing a 2,3-benzyl derivative from 1,4-dideoxy-1, 4-imino-2,3-O-isopropylidene-α-D-lyxitol or 1,4-dideoxy-1,4-imino-2,3O-isopropylidene-α-D-mannitol after removing the isopropylidene and then oxidizing the derivative to prepare a compound of the formula I wherein R$^3$ is —COOH or (CHOH)COOH, and reacting with a compound of the formula R$^2$OH or a compound of the formula I wherein R$^3$ is (CHOH)CH$_2$R and esterifying the 6-deoxy-6-halo-mannitol derivative using the methods given where a compound of the formula I is required wherein R$^3$ is (CHOR$^1$) CH$_2$R$^6$, to produce compounds of the formula I wherein R$^3$ is —COOR$^2$ or —(CHOH)COOR$^2$ and R$^2$ is as defined above;

(v) protecting the C5 position of 1,4-dideoxy-1,4-imino-2,3-O-isopropylidene-α-D-lyxitol or the C5 and C6 positions of 1,4-dideoxy-1,4-imino-2,3-O-isopropylidene-α-D-mannitol, removing the isopropylidene and then selectively esterifying by reacting with a compound of the formula

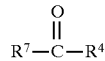

III wherein R$^7$ is a 1-oxy-benzotriazol or a halogen preferably fluorine, chlorine, iodine or bromine and R$^4$ is p-nitrobenzyl, octyl or butyl, when a compound of the formula I is required wherein R$^1$ is p-nitrobenzoyloxy, -octanoyloxy or -butanoyloxy;

(vi) oxidizing 1,4-dideoxy-1,4-imino-2,3-O-isopropylidene- α-D-lyxitol with an oxidizing agent or selectively oxidizing the primary alcohol in 1,4-dideoxy-1,4-imino-2,3-O-isopropylidene- α-D-mannitol and then reacting either with a compound of the formula R$^9$:Mg:R$^6$ wherein R$^9$ is $(C_1-C_5)$-alkyl, and R$^6$ is halogen preferably fluorine, chlorine, iodine or bromine when a compound of the formula I is required in which R$^3$ is CHR$^9$OH and R$^9$ is $(C_1-C_5)$-alkyl, or when a compound of the formula I is required wherein R$^3$ is (CHOH)CHR$^9$OH wherein R$^9$ is $(C_1-C_5)$-alkyl; and optionally when a compound of the formula I is required wherein R$^2$ is other than hydrogen, N-alkylating using the methods described above in (i); and/or where compounds of the formula I are required wherein R$^1$ is other than hydrogen esterifiying using the methods set out in (v).

The present invention also relates to a compound of the formula IV

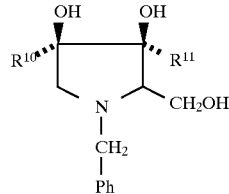

wherein R$^{10}$ and R$^{11}$ are the same or different and represent hydrogen, hydroxyl, halo, amino, alkoxy, alkyl or aryl, and Ph represents phenyl. A preferred compound of the formula IV is the compound where R$^{10}$ and R$^{11}$ are hydrogen.

The present invention also relates to the use of a compound of the formula I defined as follows as a prodrug

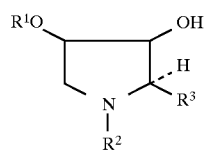

wherein

R$^1$ is hydrogen or p-nitrobenzoyloxy, octanoyloxy or -butanoyloxy;

R$^2$ is a bond, hydrogen, $(C_1-C_5)$-alkyl, methyl cyclopropane, methyl cyclohexane, tertiary butyl or benzyl;

R$^3$ is —COOR$^4$ wherein R$^4$ is p-nitrobenzyl, octyl, or butyl; as defined above; —(CHOR$^1$)COOR$^4$ wherein R$_4$ is as defined above; —CHR$^2$OR$^1$ wherein R$^1$ and R$^2$ are as defined above;

—(CHOR¹)(CHR²OR¹) wherein R¹ and R² are as defined above;

—CH₂O—CO—R⁴ wherein R⁴ is as defined above; —(CHOR¹)(CH₂R⁶) wherein

R¹ is as defined above and R⁶ is a halogen preferably fluorine, chlorine, iodine or bromine; —CH₂R⁶ wherein R⁶ is as defined above; or when R² is a bond, R₃ is —CHR⁸CH₂CH₂CH₂— which together with N forms a ring wherein R⁸ is p-nitrobenzoyloxy, anoyloxy or -butanoyloxy, with the proviso that when R¹ is hydrogen and R₃ is —(CHOH)(CH₂OH), R² cannot be methyl, n-butyl or benzyl and that when R¹ and R² are hydrogen, R₃ cannot be —CH₂OH, —(CHOH)CH₃, —(CHOH)(CH₂F) or —(CHOH)(CH₂OH). These defined compounds are also referred to herein as "compounds of Formula II".

These and other aspects of the present invention will become evident upon reference to the following detailed description and attached drawings. In addition, reference is made herein to various publications, which are hereby incorporated by reference in their entirety.

BRIEF DESCRIPTION OF THE DRAWINGS

The invention will be better understood with reference to the drawings in which.

DETAILED DESCRIPTION OF THE INVENTION

Figure 1:
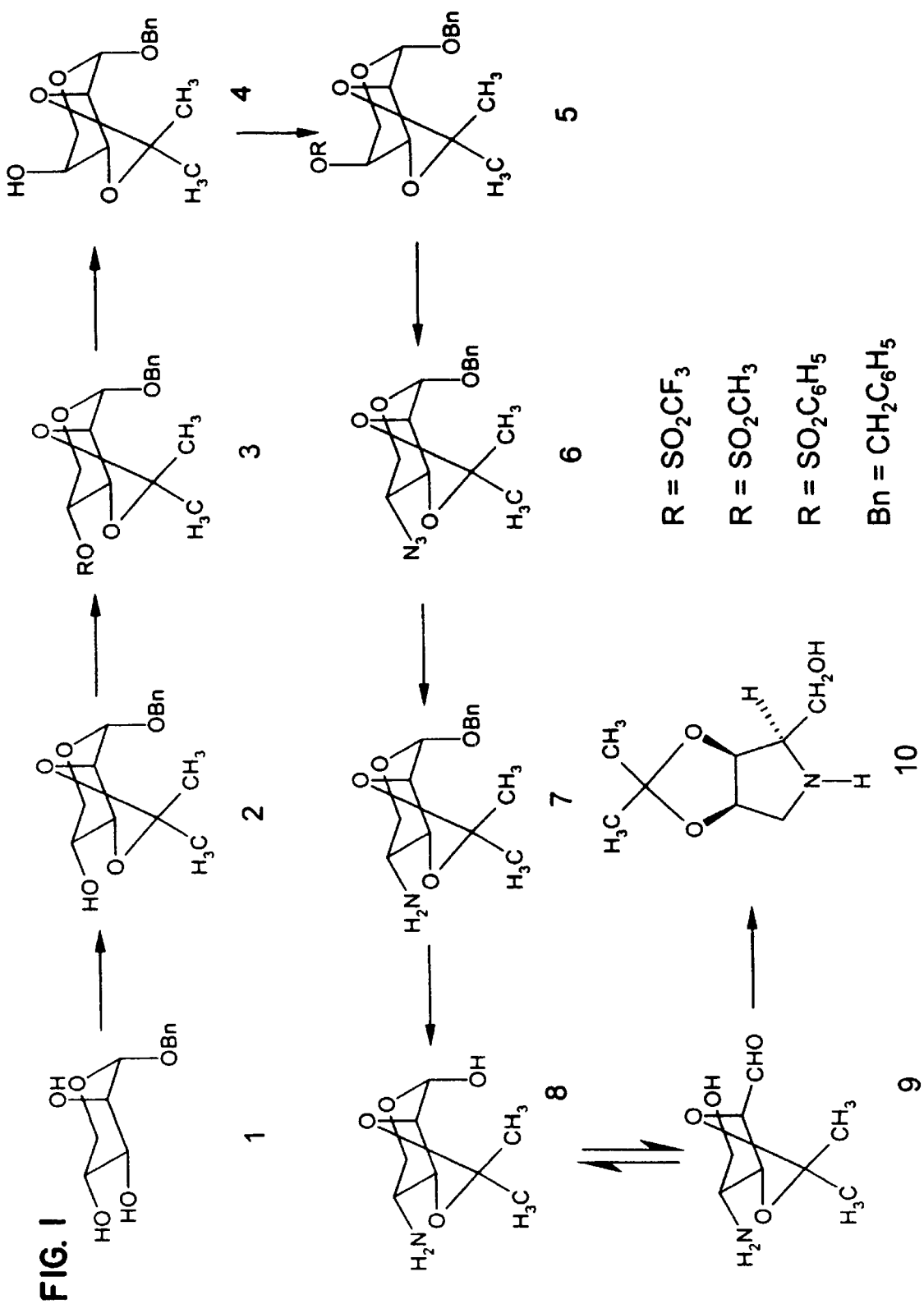
FIG. 1 is a schematic diagram of a process of the invention.

As hereinbefore mentioned the present invention relates to a compound of the formula I

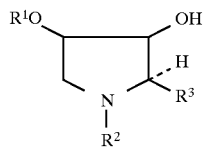

wherein
R¹ is hydrogen or p-nitrobenzoyloxy, -octanoyloxy or-butanoyloxy;

R² is hydrogen, (C₁–C₅)-alkyl, methyl cyclopropane, methyl cyclohexane, tertiary butyl or benzyl;

R³ is —COOR⁴ wherein R⁴ is p-nitrobenzyl, octyl, or butyl;

—(CHOR¹)COOR⁴ wherein R⁴ is as defined above; —CHR²OR¹ wherein R¹ and R² are as defined above; —(CHOR¹)(CHR²OR¹) wherein R¹ and R² are as defined above;

—CH₂O—CO—R⁴ wherein R⁴ is as defined above; or —(CHOR¹)(CH₂R⁶) wherein R¹ is as defined above and R⁶ is a halogen preferably fluorine, chlorine, iodine or bromine; —CH₂R⁶ wherein R⁶ is as defined above; with the proviso that when R¹ is hydrogen and R³ is —(CHOH)(CH₂OH), R² cannot be methyl, n-butyl or benzyl and that when R¹ and R² are hydrogen, R³ cannot be —CH₂OH, —(CHOH)CH₃, —(CHOH)(CH₂F) or —(CHOH)(CH₂OH).

Preferred compounds of the invention are those compounds where R² is —CH₂CH₃ and R³ is —CH(CH₃)OH, R² is —CH₂CH₂CH₃ and R³ is —CH₂OH, R₂ is —CH₃ and R³ is —CH(CH₂CH₃)OH, R² is —H and R³ is —CH(CH₂CH₂CH₃)OH, and the p-nitrobenzoyloxy,-octanoyloxy or -butanoyloxy esters thereof, preferably the above noted compounds wherein R¹ is p-nitrobenzoyloxy, -octanoyloxy or-butanoyloxy, R² is hydrogen, and R³ is —(CHOH)CH₂OH; R¹ and R² are hydrogen, and R³ is —(CHOH)CH₂OR⁸ wherein R⁸ is p-nitrobenzoyloxy,-octanoyloxy or -butanoyloxy; R¹ is p-nitrobenzoyloxy, -octanoyloxy or-butanoyloxy, R² is hydrogen, and R³ is —(CHOH)CH₂OR⁸ wherein R⁸ is p-nitrobenzoyloxy, -octanoyloxy or -butanoyloxy; R¹ and R² are hydrogen, and R³ is —COOR⁴ wherein R⁴ is p-nitrobenzyl, octyl or butyl; R¹ is p-nitrobenzoyloxy, -octanoyloxy or -butanoyloxy, R² is —CH₂CH₂CH₃, and R³ is —CH₂OH; R¹ is hydrogen, R² is —CH₂CH₂CH₃, and R³ is —CH₂OR⁸ wherein R⁸ is p-nitrobenzoyloxy, -octanoyloxy or -butanoyloxy ; R¹ is hydrogen, R² is —CH₂CH₃, and R³ is —CH(CH₃)OR⁸ wherein R⁸ is p-nitrobenzoyloxy, -octanoyloxy or -butanoyloxy; R¹ is hydrogen, R² is —CH₃, and R³ is —CH(CH₂CH₃)OR⁸ wherein R⁸ is p-nitrobenzoyloxy,-octanoyloxy or -butanoyloxy; and R¹ is hydrogen, R² is hydrogen, and R³ is —CH(CH₂CH₂CH₃)OR⁸ wherein R⁸ is p-nitrobenzoyloxy, -octanoyloxy or -butanoyloxy; and where R¹ is p-nitrobenzoyloxy, -octanoyloxy or butanoyloxy, R² is —CH₃, and R³ is —CH(CH₂CH₃)OR8 wherein R⁸ is p-nitrobenzoyloxy, -octanoyloxy or -butanoyloxy; and R1 is p-nitrobenzoyloxy, -octanoyloxy or butanoyloxy, R² is hydrogen, and R³ is —CH(CH₂CH₂CH₃)OR⁸ wherein R⁸ is p-nitrobenzoyloxy, -octanoyloxy or -butanoyloxy.

The compounds of the formula I may be present in the form of their salts when R³ contains a free carboxyl group. In general these are salts with alkali metal halides, for example, sodium chloride, sodium iodide or lithium iodide.

The compounds of the formula I are derived from 1,4-dideoxy-1,4-imino-2,3-O-isopropylidene-α-D-lyxitol which may be prepared by a novel method of the invention. The method comprises converting benzyl 2,3-O-isopropylidene-α-L- ribopyranoside by S_N2 inversion to benzyl-4-azido-4-deoxy-2,3-O- isopropylidene-α-D-lyxopyranoside and subjecting benzyl-4-azido-4-deoxy-2,3-O-isopropylidene-α-D-lyxopyranoside to intramolecular reductive amination and cyclization.

Benzyl 2,3-O-isopropylidene-α-L-ribopyranoside 4 may be obtained from benzyl-α-D-lyxopyranoside 1 as shown in the reaction scheme set out in FIG. 1. Compound 1 on acetonation in the presence of acid results in the 2,3-O- isopropylidene derivative 2, which on esterification with triflic anhydride in dichloromethane at −10° to −20° C. provides the 4-O-triflate derivative 3 in a quantitative yield. The $S_N2$ inversion at C4 of compound 3 may be achieved by treating 3 in a minimum volume of N,N-dimethylformamide with sodium nitrite at room temperature following the general procedure of Ramadan I. El-Sokkary, Basim Azmy Silwanis, Mina A. Nashed. Carbohydr. Res. 203 (1990) 319–323 to produce 4.

Benzyl 2,3-O-isopropylidene-α-L-ribopyranoside 4 is converted by $S_N2$ inversion to benzyl-4-azido-4-deoxy-2,3-O-isopropylidene-α-D-lyxopyranoside. The $S_N2$ inversion at C4 of compound 4 may be carried out by first preparing a 4-O-sulfonic ester, for example, a 4-O-triflate, 4-Omesylate or 4-O-tosylate. These esters may be used for $S_N2$ inversion with reagents such as sodium azide or tetrabutylammonium azide to produce benzyl-4-azido-4-deoxy-2,3-O-isopropylidene-a-4-lyxopyranoside 6. Treatment of the tosylate ester 4 with sodium azide in DMSO at high temperature provides a very good to excellent yield (Eugene A. Mash and Sandeep K. Nimkar. Tetrahedron Letters 34 No. 3 (1993) 385–388).

The benzyl-4-azido-4-deoxy-2,3-O-isopropylidene-α-D-lyxopyranoside 6 is subjected to intramolecular reductive amination and cyclization to produce 1,4-dideoxy-1,4-imino-2,3-O-isopropylidene-α-D-lyxitol. The intramolecular reductive animation may be carried out by treating benzyl-4-azido-4-deoxy-2,3O-isopropylidene-α-D-lyxopyranoside 6 with palladium on charcoal in methanol, under the pressure of hydrogen, to produce compound 8 with a free amino group and a free anomeric group. To improve the yield of this reaction, the reduction may be achieved by treating with sodium hydrogentelluride (NaTeH) in ethanol/ether at room temperature with high yield (Hitomi Suzuki and Koji Takaoka, Chem. Lett. (1984) 1733–1736) to produce compound 7 with only a free amino group, with subsequent catalytic hydrogenolysis of the benzyl group to produce 8. The free amine may also be obtained from azide by treatment with an alkaline earth metal (for example, magnesium or calcium), (Samarendra N. Maiti, Paul Spevak and A. V. Narender Reddy. Synthetic Communication, 18 (11), (1988) 1201–1206) in methanol at low temperatures. The compound 8 in acetic acid which is in equilibrium with the open chain amino aldehyde 9, on treatment with palladium black under the atmosphere of hydrogen, could follow by reductive amination and cyclization to provide 10.

In summary, a preferred method of the invention for producing 1,4-dideoxy-1,4-imino-2,3-O-isopropylidene-α-D-lyxitol comprises converting benzyl 2,3-O-isopropylidene-4-O-triflate-α-D-lyxopyranoside to its L-ribopyranoside form with hydroxide. The L-ribopyranoside is treated with tetra butyl ammonium azide to produce benzyl 2,3-O-isopropylidene-4-azido-4-deoxy-α-D-lyxopyranoside. The open chain aminoaldehyde form is then obtained by hydrogenolysis of the protected 4-azido benzyl lyxopyranoside with palladium on carbon in an appropriate solvent. Intramolecular reductive amination of the main aldehyde is carried out to produce 1,4-dideoxy-1,4-imino-2,3-O-isopropylidene-α-D-lyxitol. The isopropylidene protecting group is then removed to give 1,4-dideoxy-1,4-imino-D-lyxitol. This may be achieved by either treating compound 10 with trifluoroacetic acid:water at room temperature or with acetic acid:water at elevated temperatures (50°–60° C.). High yield may be achieved by treatment of the isopropylidene derivative with a dilute solution of iodine in methanol (Szarek WA et al., Tetrahedron Lett. 27, 33:3827–3830).The detailed reaction is shown in the reaction scheme in FIG. 1.

Figure 2:
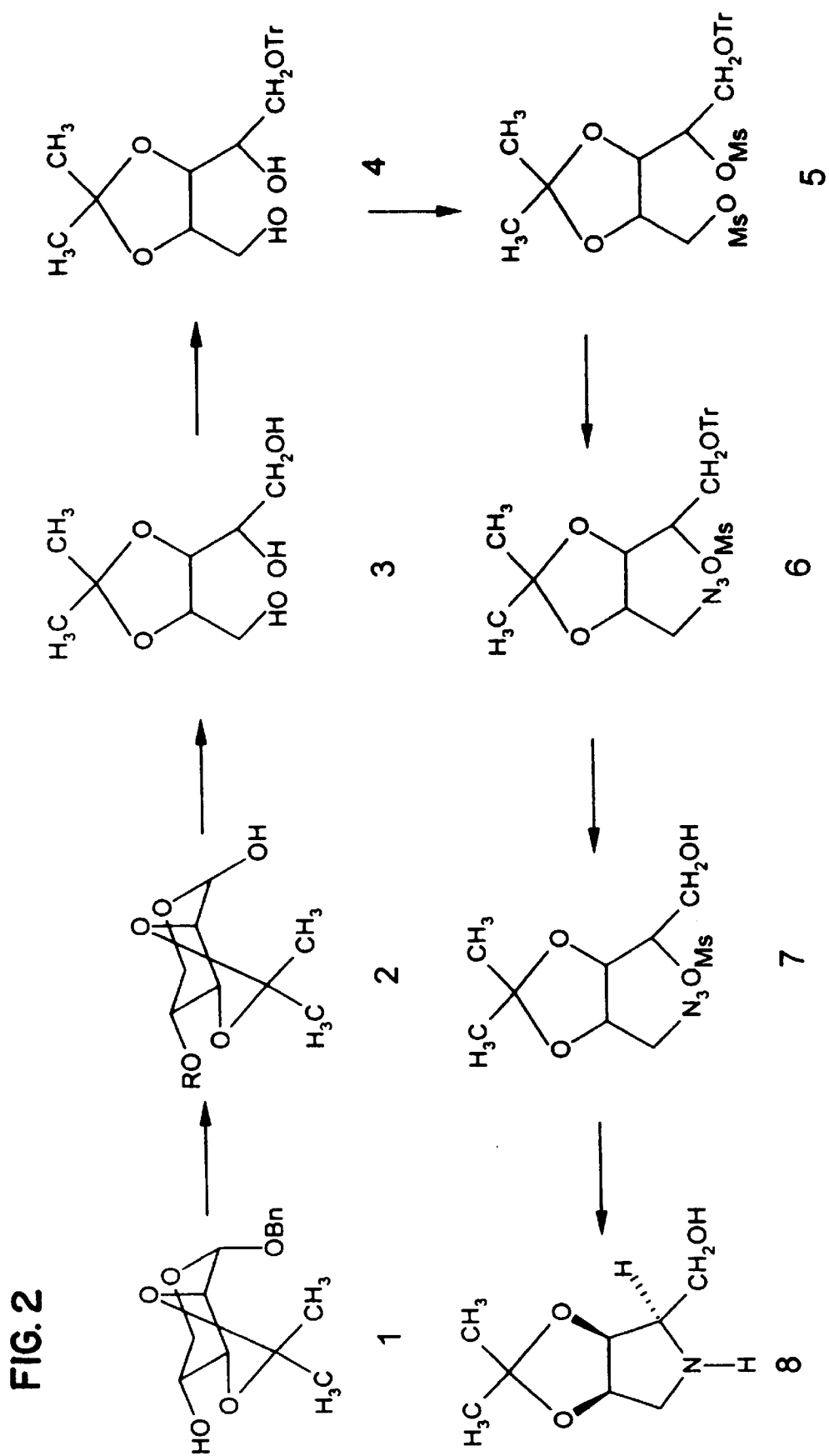
FIG. 2 is a schematic diagram of a process for preparing 1,4dideoxy-1,4imino-2,3-O-isopropylidene-α-D-lyxitol from D-lyxose.

It will be appreciated that 1,4-dideoxy-1,4-imino-2,3-O-isopropylidene-α-D-lyxitol may also be prepared by the method of Fleet G. W. J. et al., (Tetrahedron Letters, Vol.26:3127 U.S. Pat. Nos. 4,996,239 and 5,041,555). However, the Fleet method retains an additional asymmetric centre in the compound compared to the novel method of the invention and accordingly is more complex than the novel method of the present invention. 1,4-dideoxy-1,4-imino-2,3-O-isopropylidene-α-D-lyxitol may also be synthesized directly from D-lyxose using an approach similar to that described above and shown in FIG. 2.

Compounds of the formula I wherein $R^2$ is (C1–C5)-alkyl, tertiary butyl or benzyl may be prepared by N-alkylating 1,4-dideoxy-1,4-imino-2,3-O-isopropylidene-α-D-lyxitol which is protected at the C5 position under suitable conditions, with a compound of the formula $R^4CHO$ wherein $R^4$ is (C1–C5)-alkyl, tertiary butyl or benzyl. The 1,4-dideoxy-1,4-imino-2,3-O-isopropylidene-α-D-lyxitol may be protected at the C5 position using conventional techniques. For example, a 5-0-triphenylmethyl (trityl) derivative may be prepared following conventional methods by reacting 10 with trityl chloride in the presence of pyridine. Compound 10 could also be reacted with tritylpyridinium fluoroborate in acetonitrile ( S. Hanessian and A. P. A. Staub. Methods in Carbohydrate Chemistry V. p. 63–67). Some of the synthetic merits of this method are (a) shorter reaction times (b) easier workup procedures (c) compatibility of commonly utilized functional groups including acetals like isopropylidene.

As a specific example, N-propyl-1,4-dideoxy-1,4-imino-2,3-O-isopropylidene-5-O-trityl-D-lyxitol may be prepared by reacting 1,4-dideoxy-1,4-imino-2,3-O-isopropylidene-5-O-trityl-D-lyxitol in ethanol with propanal under an atmosphere of hydrogen with palladium black. Different N-alkyl derivatives may be similarly synthesized by using the corresponding alkanal.

Compounds of the formula I wherein $R^3$ is $CH_2O$—CO—$R^4$ and $R^4$ is (C1–C5)-alkyl, tertiary butyl or benzyl may be prepared by reacting 1,4-dideoxy-1,4-imino-2,3-O-isopropylidene-α-D-lyxitol with a compound of the formula $R^6$—CO—$R^4$ wherein $R^6$ is a halogen preferably fluorine, chlorine, iodine, and bromine and $R^4$ is (C1–C5)-alkyl, tertiary butyl or benzyl, under alkaline conditions. For example, 1,4dideoxy-1,4-imino-2,3-O-isopropylidene-5-O-propyloxy-lyxitol could be prepared by reacting 1,4-dideoxy-1,4-imino-2,3-isopropylidene-D-lyxitol with propionyl chloride in pyridine and dichloromethane at very low temperatures (0°–50° C.). Different 5-O-alkanoyloxy derivatives may likewise be synthesized using corresponding alkyl carbonyl chlorides.

Compounds of the formula I wherein $R^3$ is $CH_2R^6$ and $R^6$ is a halogen preferably fluorine, chlorine, iodine and bromine may be produced by reacting 1,4-dideoxy-1,4-imino-2,3-O-isopropylidene -α-D-lyxitol with triphenyl phosphine and $C(R^6)_4$ wherein $R^6$ is a halogen preferably fluorine, chlorine, iodine, and bromine under suitable conditions. The reaction preferably takes place in the presence of pyridine. For example, 5-bromo-1,4-imino-2,3-O-isopropylidene-1,4,5-trideoxy-D-lyxitol may be prepared by reacting 10 with triphenyl phosphine and carbon tetrabromide in pyridine at 0° to 50° C. Corresponding carbon tetrahalides should give corresponding halides at C5 of the D-lyxitol derivative (Roy L Whistler and Abul ashem M Anisuzzaman. Methods in Carbohydrate Chemistry. Vol. viii p. 227–321).

Compounds of the formula I wherein $R^3$ is —COOH may be produced by first preparing a 2,3-benzal derivative of 1,4-dideoxy-1,4-imino-2,3-O-isopropylidene-α-D-Iyxitol.

The isopyropylidene group is removed and the compound is then oxidized to prepare compounds of the formula I wherein $R^3$ is —COOH. The compound of the formula I wherein $R^3$ is —COOH may be synthesized by treatment of 2,3-di-O-acetyl-1,4-dideoxy-1,4-imino-D-lyxitol with an oxidizing agent such as $KMnO_4$. The carboxylic compounds may be converted to their esters by reacting with alkanol in the presence of a small quantity of acetyl chloride which also acts as an acid scavenger. For example, the compounds of the formula I wherein $R^3$ is —COOH may be reacted with propyl alcohol in the presence of acetyl chloride to give 2,3di-O-acetyl-1,4-dideoxy-1,4-imino-5-propylcarboxylate-lyxorinic acid.

The aforementioned compounds may be reacted with a compound of the formula $R^4OH$ wherein $R^4$ is (C1 –C5)- alkyl, tertiary butyl or benzyl to produce compounds of the formula I wherein $R^3$ is —$COOR^2$ and R2 is (C1–C5)-alkyl, tertiary butyl or benzyl. For example, the 2-O-butyryloxy-1,4,dideoxy-1,4-imino-2,3-O-isopropylidene-D-lyxitol may be prepared by reacting 1,4dideoxy-1,4-imino-5-O-trityl-D-lyxitol either with butyryl chloride in pyridine and dichloromethane at very low temperature (0° to –70° C.) or with 1-butyryloxy-benzotriazole in dichloromethane in the presence of triethylamine at room temperature (transesterification method (J. Org. Chem. 50 (1985) page 1752). The 2-position could also be selectively esterified by phase-transfer catalysis . (J.Garegg, Tommy Iversen and Stefan Oscarson, Carbohydr. Res. 53 (1977) C5–C7). For example, 2-butyryloxy derivatives may be prepared by treating 1,4,dideoxyl-1,4imino-5-O-trityl-D-lyxitol with butyryl chloride and tetrabutyl-ammoniumhydrogen sulphate in a mixture of dichloromethane and aqueous sodium hydroxide solution at room temperature to 45° C.

Compounds of the formula I wherein $R^1$ is p-nitrobenzoyloxy, -octanoyloxy or -butanoyloxy may be prepared by protecting the C5 position of 1,4-dideoxy-1,4-imino-2,3-O-isopropylidene-α-D-lyxitol and selectively esterifying the protected compound by reacting with a compound of the formula $R^7$—CO—$R^8$ wherein $R^7$ is benzotriazole or $R^6$ which is halogen (CL, Br, I) and $R^8$ is p-nitrobenzoyloxy, 2-octanoyloxy or 2-butanoyloxy. The method is either a transesterification or phase transfer esterification. The C5 position of 1,4-dideoxy-1,4-imino-2,3-O-isopropylidene-α-D-lyxitol may be protected as described in detail above.

Compounds of the formula I wherein $R^3$ is $CHR^9OH$ and $R^9$ is (C1–C5)-alkyl may be prepared by reacting 1,4-dideoxy-1,4-imino-2,3-O-isopropylidene-α-D-lyxitol with an oxidizing agent and then with a compound of the formula $R^9:MgR^6$ wherein $R^9$ is (C1–C5)-alkyl. For example, 1,4-imino-2,3-O-isopropylidene-6-propyl-1,4,6-trideoxy-D-mannitol may be prepared by first oxidizing 1,4-dideoxy-1,4-imino-2,3-O-isopropylidene-D-lyxitol with either DMSO (Roger F. Butterworth and Stephen Hanessian Synthesis, (1971) 70–88) based oxidation or with TPAP (tetra-n-propyl-ammonium) (Perruthenate, William P.Griffith and Steven V. Ley. Aldrichimica Acta, 23, No. 1 (1990) 13–19) based oxidation to its aldehyde derivative. Treatment with $R^9$ $MgR^6$ in ether (where $R^9$ is butyl and $R^6$ is halide such as iodine) will provide a 6-deoxy-6-propyl-D-mannitol derivative. The other 6-alkyl-6-deoxy derivatives can be prepared by using corresponding Grignard reagents.

The preferred compounds previously described may be synthesized by selecting the appropriate methods described in detail above. For example, preferred compounds of the formula I where $R^2$ is —$CH_2CH_2CH_3$, $R^1$ is octanoyloxy and $R^3$ is $CH_2OH$ may be synthesized by first reacting 1,4-dideoxy-1,4imino-2,3-O-isopropylidene-α-D-lyxitol with trityl pyridium fluoroborate in acetonitrile to afford its 5-0-trityl derivative. This reaction conducted with palladium on charcoal under an atmosphere of $H_2$ in the presence of propanol will afford N-propyl-5-0-trityl derivatives. After removing the isopropylidene group from this derivative by stirring with iodine in methanol, the compound may be selectively esterified with an octyl group using the corresponding reagent (described previously) having an octyl group. The removal of the trityl group would give the required preferred compound.

The preferred compounds with α-D-mannitol as a basic unit could be synthesized by following the general procedures used for lyxitol. The starting compound namely 1,4-dideoxy-1,4-imino-2,3-O-isopropylidene-α-D-mannitol may be synthesized using art recognized methods such as described by George W. J. Fleet et al., J. Chem. Soc. Chem. Commun. (1984) 1240–1241.

The present inventon also relates to a compound of the formula IV

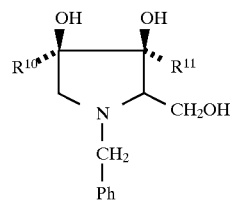

wherein $R^{10}$ and $R^{11}$ are the same or different and represent hydrogen, hydroxyl, halo, amino, alkoxy, alkyl or aryl, and Ph represents phenyl. As used herein, the term "alkyl" refers to a straight or branched chain hydrocarbon containing no unsaturation and having 1 to 4 carbon atoms. Examples of alkyl groups include methyl, ethyl, 1-propyl, 2-propyl, 1-butyl, methylcyclopropyl, and cyclobutyl. The term "aryl" used herein refers to radicals having the ring structure characteristic of benzene. Examples of aryl groups include benzyl, p-$NO_2$-benzyl, and p-methoxybenzly. The term "alkoxy" refers to a substituent which consists of an alkyl or aryl linked through an ether oxygen having its free valence bond from the ether oxygen. Examples of alkoxy groups include O-methyl, O-allyl, O-propyl, O-benzyl, O-p-$NO_2$-benzyl and O-p-methylbenzyl. methylbenzyl. The term "halogen" refers to a member of the family fluorine, chlorine, bromine, or iodine.

A preferred compound of the formula IV is the compound where $R^{10}$ and $R^{11}$ are hydrogen.

The compounds of the formula IV may be prepared by standard processes which are generally known in the art. For example, a compound of the formula IV wherein either or both of $R^{10}$ or $R^{11}$ are either alkyl or aryl may be prepared by reacting a compound of the formula V

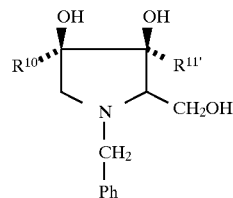

wherein $R^{10'}$ and $R^{11'}$ are hydrogen, which are appropriately blocked, and are oxidized with appropriate oxidizing agents, and then treated with appropriate Grignard reagents, followed by deblocking of the blocked groups to produce a compound of the formula IV wherein either or both of R10 and R11 is alkyl or aryl. The blocking may be accomplished using appropriate protective groups. Appropriate blocking and deblocking schemes are well known (see for example, T. W. Greene, Protective Groups in Organic Synthesis, John Wiley & Sons, New York, 1981). For example, ether, acetals, ketals, and esters may be used to protected isolated hydroxyl groups. In particular, suitable protective groups which may be used include -benzyl, O-p-methoxybenzyl, O-acetoxy, O-haloacetoxy, O-benzoyloxy and O-allyl. Removal of the protective groups may be accomplished by known methods in the art.

Alternatively, a compound of the formula IV, wherein $R^{10}$ or $R^{11}$ are either or both alkoxy, amino, or halo may be prepared from a compound of the formula V, wherein $R^{10'}$ and $R^{11'}$ are hydroxyl. The compound V is selectively appropriately blocked, and $R^{10'}$ and $R^{11'}$ may then be selectively substituted with the desired alkoxy, halo, or amino group, by methods which are known in the art.

A free hydroxyl group may easily be replaced by an alkoxy, halo or amino group in the blocked/deblocked compounds of the formula V and various derivatives of compounds of the formula IV, as is well known to the skilled artisan. In particular, a free hydroxyl group may be converted to an alkoxy group by reacting the free hydroxyl with alkyl or aryl halide in the presence of a base. A free hydroxyl group may be replaced by a halo group by first reacting the free hydroxyl group with triflic anhydride, mesyl chloride or tosyl chloride, in the presence of a base like pyridine, to block the hydroxyl with a leaving group such as triflate, mesyl, or tosyl, respectively. The blocked hydroxyl may then replaced by O-benzoate, with inversion, by treatment with sodium benzoate in DMF. The O-benzoate is then de-esterified, blocked again with a suitable leaving group, and on treatment with tetrabutylammonium halide, is replaced with inversion, by the respective halide, or on treatment with sodium azide is replaced, with inversion, by azido, and subsequently by amino on reduction. These methods are well known to one skilled in the art.

If necessary, the products of the processes described above may be purified by conventional methods such as column chromatography.

The compounds of the formula I described above may be converted into salts by reaction with an alkali metal halide, for example, sodium chloride, sodium iodide or lithium iodide. Preferably, the compounds of the formula I are converted into their salts by reaction with a stoichiometric amount of sodium chloride in the presence of a solvent such as acetone. The conversion to the corresponding salts is generally carried out in the temperature range $-20°$ C. to $80°$ C. and the reaction times are between about 1 to 12 hours.

The compounds of the formula II include compounds of the formula I as described above and compounds of the formula Ia wherein $R^1$ is hydrogen, $R^2$ is a bond and $R^3$ is —$CHR^8CH_2CH_2CH_2$ which together with N forms a ring wherein $R^8$ is p-nitrobenzoyloxy, -octanoyloxy or-butanoyloxy. The compounds of the formula Ia may be derived from swainsonine. Swainsonine may be prepared using methods known in the art such as described by Bennett R. B., et al, J. Am. Chem. Soc. 1989, 111, 2580–2582. Swainsonine may then be converted into compounds of the formula Ia by conventional methods.

The compounds of the formula I, II and IV are inhibitors of oligosaccharide processing and in particular are inhibitors of mannosidase. General mannosidase inhibition may be tested by measuring the inhibition of Jack Bean α-mannosidase and lysosomal α-mannosidase. However, the specific binding of the toxic plant lectin L-PHA to transformed cell lines such as MDAY-D2 tumor cells, has been found to more specifically measure inhibition of oligosaccharide processing. The present inventors have also found that the measurement of $IC_{50}$ in this L-PHA toxicity assay reflects the ability of the compound to enter into cells and to effect inhibition of oligosaccharide processing. It is therefore a general screen for activity in cells which measures cell entry, inhibition of the target enzyme, α-mannosidase II in the Golgi, and the resulting cellular phenotype.

Thus, the invention also provides a method for testing a substance for its ability to inhibit N-linked oligosaccharide processing comprising reacting the substance with a transformed cell in the presence of L-PHA and measuring the ability of the substance to inhibit the binding of L-PHA to transformed cells. The method may be used to identify substances which inhibit all steps in the N-linked oligosaccharide pathway prior to β1–4 Gal-transferase.

Other target enzymes for which inhibitors can be tested using the L-PHA toxicity assay are those earlier on in the N-linked processing pathway which block the biosynthesis of the L-PHA binding structure. These are tri-and tetra-antennary complex type oligosaccharides having the sequence

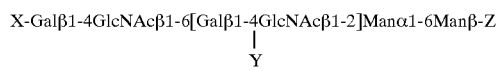

where X and Y can be sialic acid, fucose, N-acetylglucose amine galactose and $SO_4$ and Z is a glycan sequence linked to the asparagine of glycoproteins. These enzyme targets include GlcNAc-TI, GlcNAc-II, β1–4Gal-T, and UDP-Gal transporter in the Golgi.

In one embodiment of the invention a method is provided for testing a substance for its ability to inhibit N-linked oligosaccharide processing comprising growing transformed cells in the presence of L-PHA and the substance; measuring the amount of proliferation of the cells; and determining the ability of the substance to inhibit N-linked oligosaccharide processing by comparing the amount of proliferation of the cells with the amount of proliferation observed for the cells grown in the presence of L-PHA alone.

Transformed cells which may be used in the method include MDAY-D2, L1210, CHO, B16, melanoma tumor cells, and human tumor cells such as SW 480, LS174T, HT-29, WiDr, T2, MDA-231, MCF7, BT-20, Hs578T, K562, Hs578T, SK-BR-3, CY 6T, MDA-468, H23, H157, H358, H1334, H1155, H28, H460, Hmesol, H187, H510A, N417, H146, H1092, H82 (Restifo, N. P. et al, J. Exper. Med. 177:265–272,1993).

The amount of proliferation of the cells may be measured using conventional techniques. For example, cell proliferation may be measured by measuring incorporation of labeled thymidine. More particularly, radioactively labeled thymidine may be added for about 2–5 hours, preferably 3–4 hours and the cells can be harvested and radioactivity counted using a scintillation counter.

The conditions for carrying out the method of the invention will be selected having regard to the nature of the substance and the cells employed. For example, if the transformed cells are MDAY-D2 tumor cells a concentration of about $1-4\times10^4$ cells, preferably $2\times10^4$ may be used. The MDAY-D2 cells are generally cultured for about 10 to 30 hours, preferably 18 to 20 hours, followed by addition of L-PHA at a concentration of about 10–50 µg/ml preferably 20–30 µ/ml, most preferably 25 µg/ml.

The ability of the compounds of the formulae I, II, IV or other putative inhibitors of oligosaccharide processing to be converted into more active compounds in cells can be measured by performing the L-PHA toxicity assay in the presence of an esterase inhibitor such as diethyl p-nitrophenyl phosphate. An increase in $IC_{50}$ in the L-PHA toxicity assay in the presence of diethyl p-nitrophenyl phosphate suggests that the compound requires activation by esterases and would accordingly be useful as a prodrug.

Thus, the invention also provides a method for identifying a substance which can be used as a prodrug which inhibits N-linked oligosaccharide processing comprising reacting the substance with an esterase inhibitor in an L-PHA toxicity assay. The method may be used to screen for prodrugs and can be used to identify substances which inhibit all steps in the N-linked oligosaccharide pathway prior to β1–4 Gal-transferase as described above.

In one embodiment of the invention a method is provided for identifying a substance which can be used as prodrug which inhibits N-linked oligosaccharide processing comprising growing transformed cells in the presence of L-PHA, the substance and an esterase inhibitor; measuring the amount of proliferation of the cells; and comparing the amount of proliferation of the cells with the amount of proliferation observed for the cells grown in the presence of L-PHA and the substance alone.

The compounds of the formula I, II, and IV have valuable pharmacological properties. In particular, the compounds have immunostimulatory, antimicrobial and anti-cancer effects. The anti-cancer effects of the compounds may be demonstrated using a lung colonization assay. For example, melanoma cells treated with a compound may be injected into mice and the ability of the melanoma cells to colonize the lungs of the mice may be examined by counting tumor nodules on the lung after death. Suppression of tumor growth in mice by the compound administered orally or intravenously may be examined by measuring tumor volume.

The compounds of the formula I, II and IV may be used to stimulate bone marrow cell proliferation. The myeloproliferative activity of a compound of the formula I, II, or IV may be determined by injecting the compound into mice, sacrificing the mice, removing bone marrow cells and measuring the ability of the compound to stimulate bone marrow proliferation by directly counting BM cells and by measuring clonogenic progenitor cells in methylcellulose assays.

As immunostimulatory substances the compounds of the formula I, II, and IV may be used in cases where the patient has been immunocompromised such as patients infected with HIV and other viruses or infectious agents, in patients undergoing bone marrow transplants, and in patients having various cancers. The compounds also have an antiviral effect in particular on membrane enveloped viruses such as retroviruses, influenza viruses, cytomegaloviruses and herpes viruses. The compounds are also useful in the prevention, treatment and prophylaxis of metastasis of tumors.

The compounds may be especially useful in the treatment of various forms of neoplasia such as leukemias, lymphomas, melanomas, adenomas, sarcomas, and carcinomas of solid tissues. In particular the composition may be useful for treating malignant melanoma, pancreatic cancer, cervico-uterine cancer, cancer of the kidney, stomach, lung, rectum, breast, bowel, gastric, liver, thyroid, neck, cervix, salivary gland, leg, tongue, lip, bile duct, pelvis, mediastinum, urethra, bronchogenic, bladder, esophagus and colon, and Kaposi's Sarcoma which is a form of cancer associated with HIV-infected patients with Acquired Immune Deficiency Syndrome (AIDS). The compounds may also be used for other antiproliferative conditions such as arthrosclerosis and viral infections, in particular AIDS.

The compounds may be converted using customary methods into pharmaceutical compositions. The pharmaceutical compositions contain the compounds either alone or together with other active substances. Such pharmaceutical compositions can be for oral, topical, rectal, parenteral, local, inhalant, or intracerebral use. They are therefore in solid or semisolid form, for example pills, tablets, creams, gelatin capsules, capsules, liposomes (See U.S. patent application Ser. No. 5,376,452) suppositories, soft gelatin capsules, gels, membranes, and tubelets. For parenteral and intracerebral uses, those forms for intramuscular or subcutaneous administration can be used, or forms for infusion or intravenous or intracerebral injection can be used, and can therefore be prepared as solutions of the compounds or as powders of the active compounds to be mixed with one or more pharmaceutically acceptable excipients or diluents, suitable for the aforesaid uses and with an osmolarity which is compatible with the physiological fluids. For local use, those preparations in the form of creams or ointments for topical use or in the form of sprays should be considered; for inhalant uses, preparations in the form of sprays, for example nose sprays, should be considered.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the pharmaceutical compositions include, albeit not exclusively, the compounds in association with one or more pharmaceutically acceptable vehicles or diluents, and contained in buffered solutions with a suitable pH and iso-osmotic with the physiological fluids.

The compounds are indicated as therapeutic agents either alone or in conjunction with other therapeutic agents or other forms of treatment. The compositions and agents of the invention can be intended for administration to humans or animals.

In general, a dosage range of the compounds in the composition is envisaged for administration in human medicine of from about 0.01 to 20 mg/kg of body weight daily. In the case of parenteral compositions of this invention, the dosage is about 0.5 to about 25% by weight of the compounds in solution.

Amounts of drug administered to produce serum levels 10–1000×the $IC_{50}$ for inhibition of oligosaccharide processing in the L-PHA assay are preferably employed.

It will also be appreciated that it may be necessary to deviate from the amounts mentioned and in particular to do so as a function of the body weight of the animal to be treated, the particular disease to be treated, the nature of the administration route and the therapy desired. In addition, the type of animal and its individual behaviour towards the medicine or the nature of its formulation and the time or interval at which it is administered may also indicate use of amounts different from those mentioned. Thus it may suffice, in some cases, to manage with less than the above-mentioned minimum amounts whilst in other cases the upper limit mentioned must be exceeded. Where major amounts are administered, it may be advisable to divide these into several administrations over the course of the day.

The following examples are offered by way of illustration, and not by way of limitation.

EXAMPLES

Example 1

A series of SW analogues were chemically synthesized and compared for inhibition of complex-type N-linked oligosaccharide processing in cultured MDAY-D2 tumor cells, for inhibition of α-mannosidases in vitro, cell entry and inhibition of oligosaccharide processing in cells, inhibition of cancer metastasis, and stimulation of bone marrow proliferation in vivo.

The following materials and methods were used in the investigations outlined in the Example:

MATERIAL AND METHODS

Figure 3:
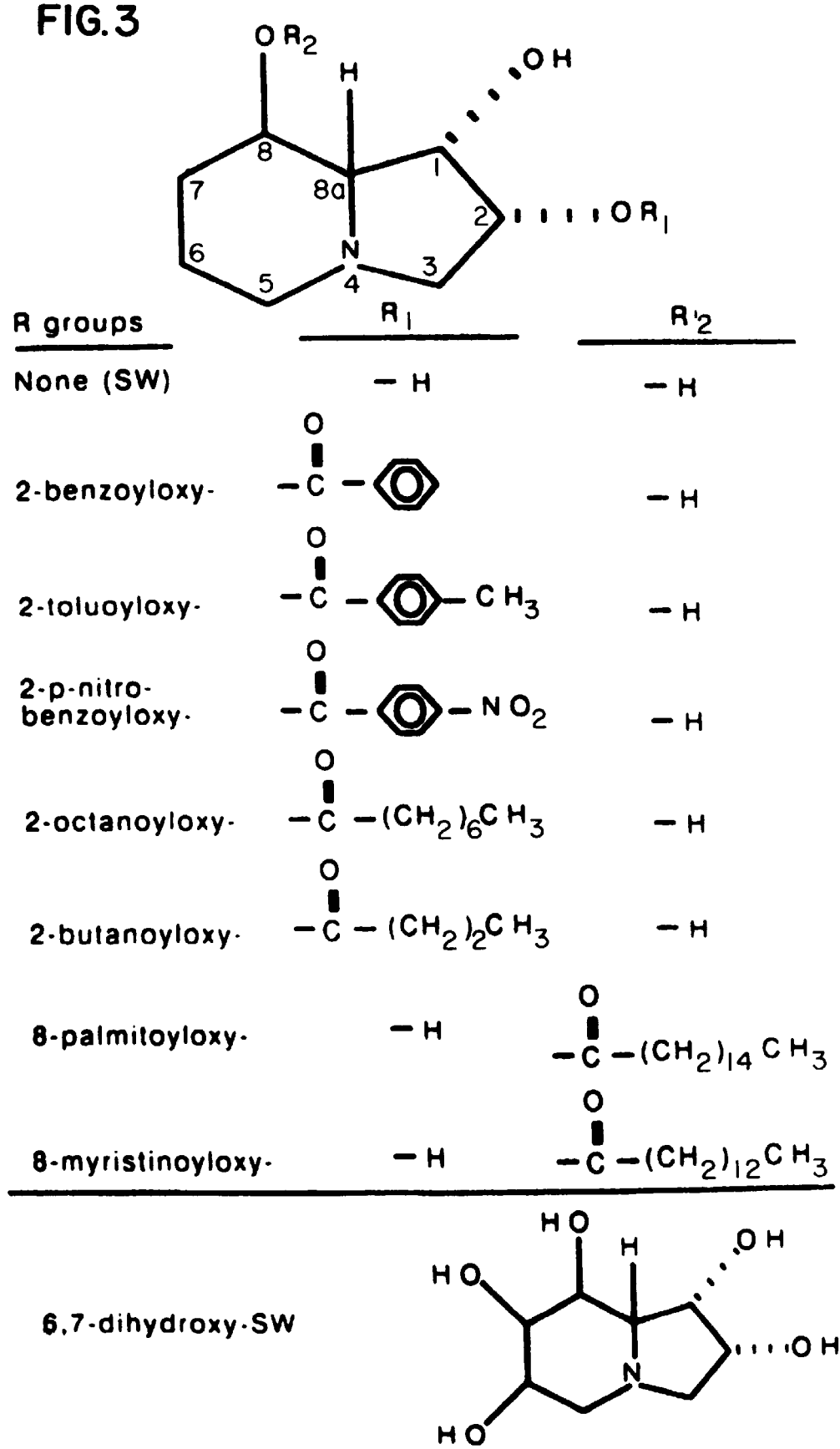
FIG. 3 shows the structure of SW and analogues.

Analogues of SW were synthesized by Toronto Research Chemicals (Toronto, Canada) and included 2-benzoyloxy-SW, 2-toluoyloxy-SW, 2-p-nitrobenzoyloxy-SW, 2-octanoyloxy-SW, 2-butanoyloxy-SW. 8-palmitoyloxy-SW, 8-myristinoyloxy-SW, 6,7-dihydroxy-SW (FIG. 3). The structures of all new compounds utilized were confirmed by proton nuclear magnetic resonance (NMR) spectroscopic analysis, using a combination of 2D COSY experiments which allowed unambiguous assignment of the 1D spectras and by Rotating Frame NOE spectroscopy (ROESY) experiments using methods previously described (Zhuang D. et al., Glycobiology 1:425, 1991). Chemical shifts were also obtained for intermediates in the chemical synthesis of the analogue. The analogues were purified by recrystallization to constant melting point, and purity was confirmed by NMR to be greater than 98%. Chemically synthesized SW and the natural product from *Rhizoctonia leguminicola* have previously been shown to be equally effective immunomodulators (Humphries, M. J. et al, Cancer Res. 48:1410, 1988 and White SL et al, Biochem Biophys. Res. Commun 150:615–625, 1988). SW isolated from *Rhizoctonia leguminicola* by Drs. Warren Croom and Winston Hagler (North Carolina State University) was used in the bone marrow (BM) proliferation assays and chemically synthesized SW in all other experiments. L-PHA (i.e., leukoagglutinin) was purchased from Pharmacia and $^3$H-thymidine from Amersham. Jack bean α-mannosidase and diethyl p-nitrophenyl phosphate were obtained from Sigma.

MDAY-D2 is a highly metastatic DBA/2 strain lymphoreticular tumor cell line (Kerbel, RS et al, J. NAtl. Cancer Inst. 64:1221–1230, 1980), and B16F10 is a metastatic subline of the C57B1/6j strain melanoma (Fidler IJ, Nature New Biol., 242:148–149, 1973). Tumor cells were grown in Modified Eagles Medium (MEM) plus 10% fetal calf serum (FCS).

Inhibition of Jack Bean and Lysosomal α-Mannosidases by SW and Aanalogues

SW and analogues were serially diluted into a volume of 75 µl in 96 well Elisa plates followed by the addition of 37.5 µl of 100 mM sodium acetate pH 5.0 and 37.5 µl of 10 mM p-nitrophenyl α-D-mannospyranoside. Jack Bean α-mannosidase (Sigma, 38 U/ml) was diluted 1/800, 10 µl was added to each well and the plates were incubated for 20 min at 37° C. The reaction was stopped by the addition of 150 µl of 0.5M sodium carbonate and formation of p-nitrophenol was measured with a plate set at 405 nm. The effects of SW and analogues on cellular acid α-mannosidases (ie. lysosomal enzyme) were measured using the same assay where Jack Bean α-mannosidase was replaced by 10 µl MDAY-D2 tumor cell lysate (10 µg/µl of protein) prepared in 0.9% NaCl, 50 mM Tris pH 7.0, 0.5% Triton X-100 and 1.0 mM diethyl p-nitrophenyl phosphate.

Inhibition of L-PHA Toxicity by SW and Analogues

MDAY-D2 tumor cells were inoculated into 96 well micro-test plates at 2×10$^4$ cells/well, and containing serial dilutions of SW or SW analogues in MEM plus 10% FCS. The cells were cultured for 18–20 hr, followed by the addition of L-PHA at 25 µg/ml for an additional 24 hr. Cell proliferation was measured by adding 0.5 µCi/well of $^3$H-thymidine for 3–4 hr, harvesting onto glass fibre disks using a Titertek harvester and the disks were counted in a liquid scintillation counter. The apparent IC$_{50}$ values for SW and the analogues are the drug concentrations showing 50% protection from L-PHA toxicity; that is 50% $^3$H-thymidine incorporated compared with cells grown in the absence of L-PHA. In experiments using the esterase inhibitor diethyl p-nitrophenyl phosphate, the compound was added to MDAY-D2 cells 4 hr prior to the α-mannosidase inhibitors and was present through-out the experiment.

Lung Colonization Assay

B16F10 melanoma cells were maintained in log-phase growth in MEM plus 10% FCS (Gibco) either untreated or treated for 48 hr with SW or analogues of SW. Cells were harvested with trypsin/EDTA (Gibco), washed and 10$^5$ melanoma cells in 100 µl of phosphate buffered saline (PBS) were injected into the lateral tail vein of male C57B1/6J mice. The lungs were removed from the mice and tumor nodules were counted at death or on day 28 when the experiment was terminated.

Bone Marrow Cell Proliferation Assay

Pathogen-free C57B1/6J mice, 8–14 weeks old were maintained according to NIH ethical guidelines. Groups of 2–3 mice received intraperitoneal injections of the PBS, SW or designated analog twice daily for 4 days. As has been reported for swainsonine (White et al., Cancer Commun., 3:83–91, 1991), 10 µg was found to be the optimal dose for all of the responsive analogues. Eighteen hours after the last SW injection, mice were sacrificed and BM cells were harvested. Marrow cell suspensions were prepared under sterile conditions using femurs and tibias of both legs from each donor. Bone marrow (BM) cells were flushed from the marrow cavities with ice-cold RPMI 1640, washed and resuspended at desired concentrations in RPMI-1640 supplemented with 5% FCS, penicillin (100 U/ml) and streptomycin (100 µg/ml). Cell viability was monitored by staining with trypan blue. The ability of the analogues to stimulate BM proliferation was measured by two methods. First, cellularity was determined by directly counting BM cells after they were flushed from the tibias and femurs. Second, enhancement in proliferation was assessed by the increase in the proportion of BM progenitor cells present in the BM preparations as measured by colony formation in soft agar (CFU). BM cells were processed according to the procedures of the GIBCO-BRL Mouse Bone Marrow Stem Cell Proliferation Kit, which employs suspensions of mononuclear cells in a semi-solid methylcellulose medium containing FCS. 2-mercaptoethanol and the growth factors, interleukin-3 (IL-3) (75 U/ml) and erythropoietin (20 U/ml). The plates were incubated for 10–14 days at 37° C. in a humidified atmosphere of 5% CO$_2$ and 95% air, and colonies consisting of at least 40 cells were enumerated using an inverted microscope. The potential colonies that form in the semi-solid medium are the granulocyte, erythrocyte, monocyte, megakaryocyte (ie. CFU-GEMM); the granulocyte, macrophage (ie. CFU-GM), and the burst forming unit-erythroid (ie BFUe).

RESULTS

The toxic plant-lectin L-PHA binds to complex-type N-linked oligosaccharides and requires the underlined portion of the structure shown below (Cummings et al., J. Biol. Chem. 257:11230–11234, 1982).

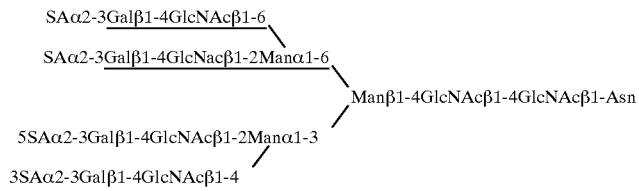

Golgi α-mannosidase II removes the underlined mannose residues in the structure shown below, allowing Golgi processing to proceed to complex-type orgosaccharides of the type shown above (Kornfeld, R. and Kornfeld, S., Annu. Rev. Biochem., 54:631–664, 1985). In SW-treated cells, this enzyme is blocked, and therefore complex-type structures are replaced by hybrid-type oligosaccharides (Tulsiani et al., J. Biol. Chem. 257:7936–7939, 1982) (see below) which lack the L-PHA reactive sequence. SAα-Galβ1–4 is added to the lower arm t complete the hybrid structure observed in SW-treated cells.

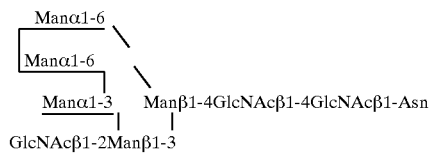

Figure 4:
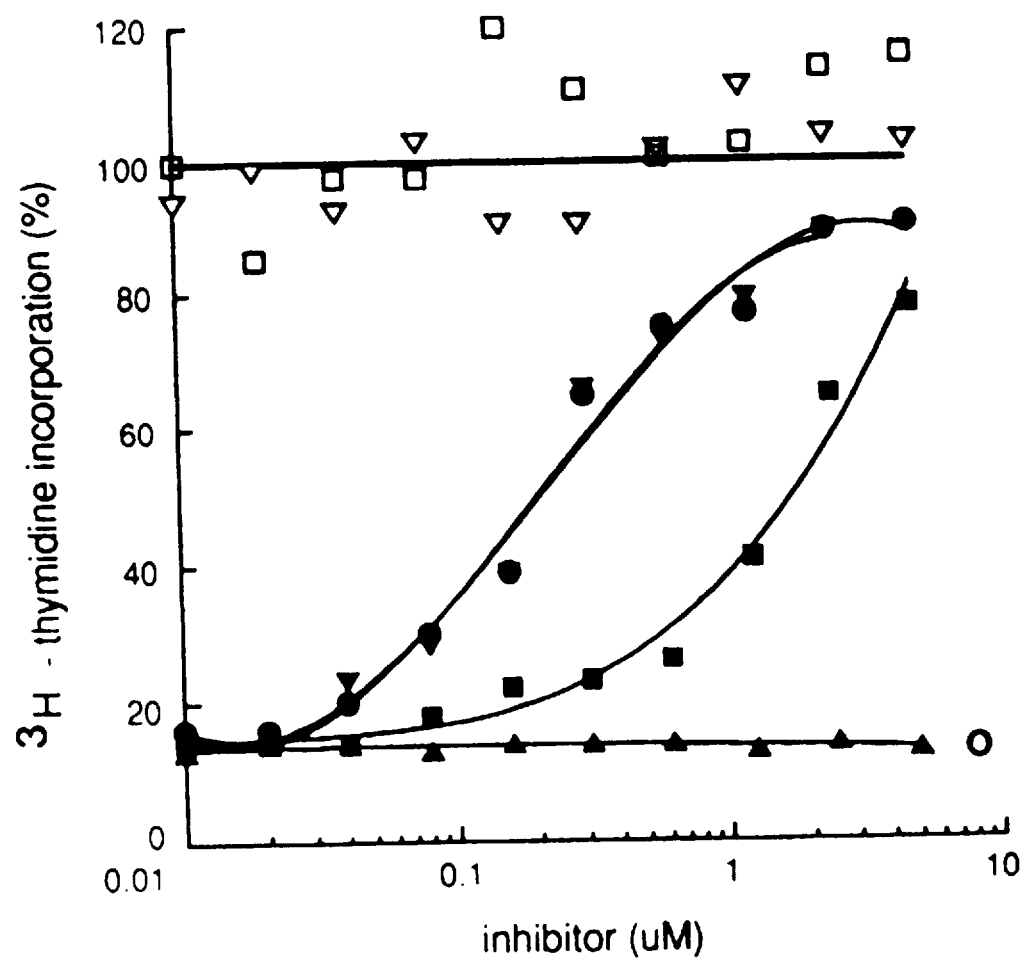
FIG. 4 is a graph showing L-PHA sensitivity of MDAY-D2 tumor cells cultured in the presence of SW, (●); 2-octanoyloxy-SW, (▼); 2-benzoyloxy-SW, (■) 8-myristinoyloxy-SW, (▲)

Consequently, cells cultured in the presence of SW show greatly reduced L-PHA binding, and increased resistance to the toxic effects of the L-PHA. The $D_{50}$ for L-PHA toxicity on MDAY-D2 cells is 5 μg/ml, whereas cells cultured in the presence of SW are resistant to >100 μg/ml of L-PHA (Dennis J. W., Cancer Res. 46:5131–5136, 1986). To compare SW and the carboxoyloxy analogues of SW for inhibition of oligosaccharide processing (ie. Golgi α-mannosidase II) in viable cells, the drugs were titrated into cultures to determine the concentration that is required to protect MDAY-D2 cells from 25 μg/ml of L-PHA (FIG. 4 is a graph showing L-PHA sensitivity of MDAY-D2 tumor cells cultured in the presence of SW, (●); 2-octanoyloxy-SW, (▼); 2-benzoylox-SW, (∪) and 8-myristinoyloxy-SW, (▲). SW and analogues in the absence of L-PHA had no effect on cell growth; open symbols are examples showing SW and 2 octanoylox-SW in the absence of L-PHA. L-PHA sensitivity in the absence of drug is shown by *.). The apparent $IC_{50}$ for SW was 0.20 μM, and the value for the SW analogues ranged from 0.23 to >5.0 μM (Table 1).

Figure 5:
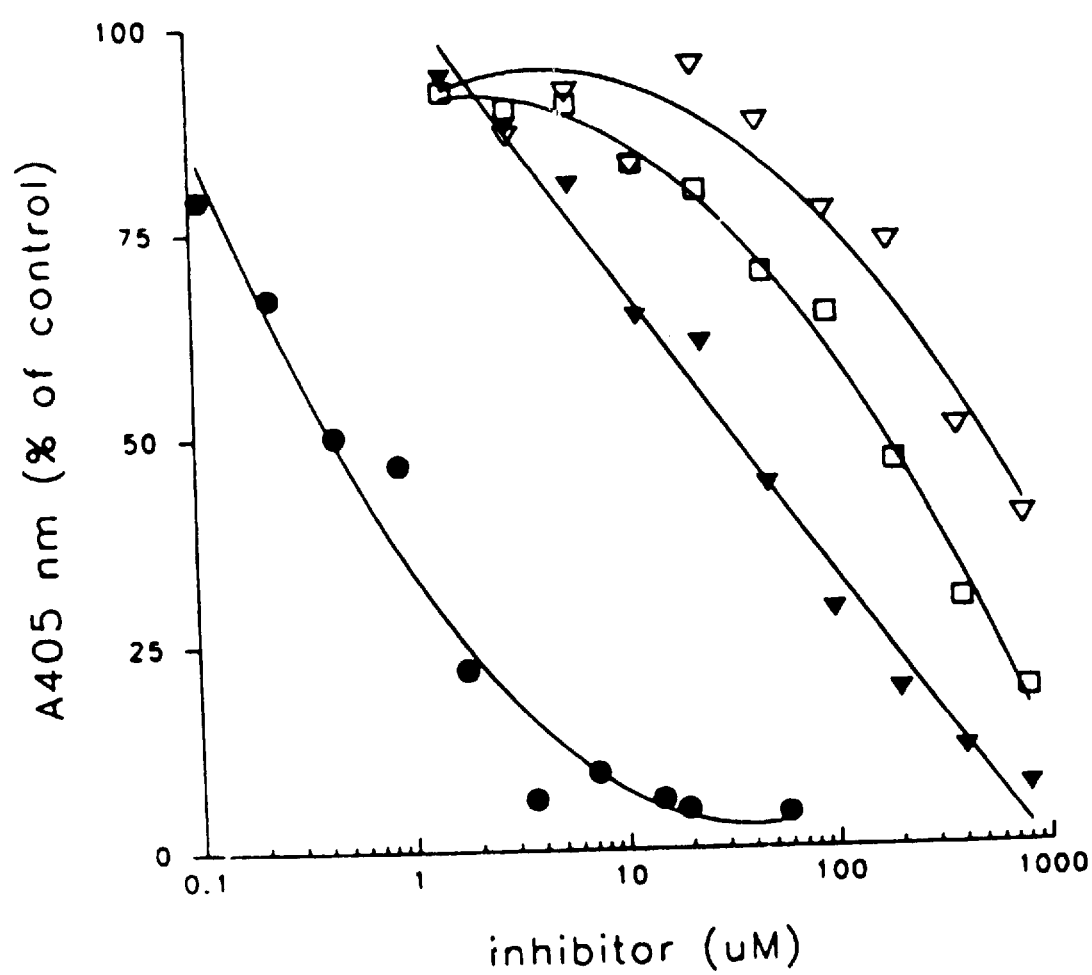
FIG. 5 is a graph showing inhibition of Jack Bean α-mannosidase by SW, (●); 2-toluoyloxy-SW, (∇); 2-butanoyloxy-SW, (□); and 6,7-dihydroxy-, (▼).

Measurement of $IC_{50}$ in the 1-PHA toxicity assay is a compilation of drug entry into the cells, potency as an α-mannosidase inhibitor, and drug catabolism and efflux from the cells. To determine whether $IC_{50}$ of the analogues in the L-PHA assay correlated with inhibitor potencies, the compounds were compared as inhibitors of Jack Bean α-mannosidase in vitro (FIG. 5). The carbonoyloxy substitutions of SW at carbons 2 or 8 greatly reduced inhibitor activity (ie. 300 to >1000 fold compared to SW) (Table 1). Although, 6,7 hydroxy-SW, was the most active of the analogues in the Jack Bean α-mannosidase assay, it was 100 times less active than SW. Inhibition by the analogues of lysosomal or-mannosidases in lysates of MDAY-D2 tumor cells (i.e. activity measured at pH 5.0) showed a similar rank order of activity as that observed for the Jack Bean enzyme (Table 1).

Figure 6:
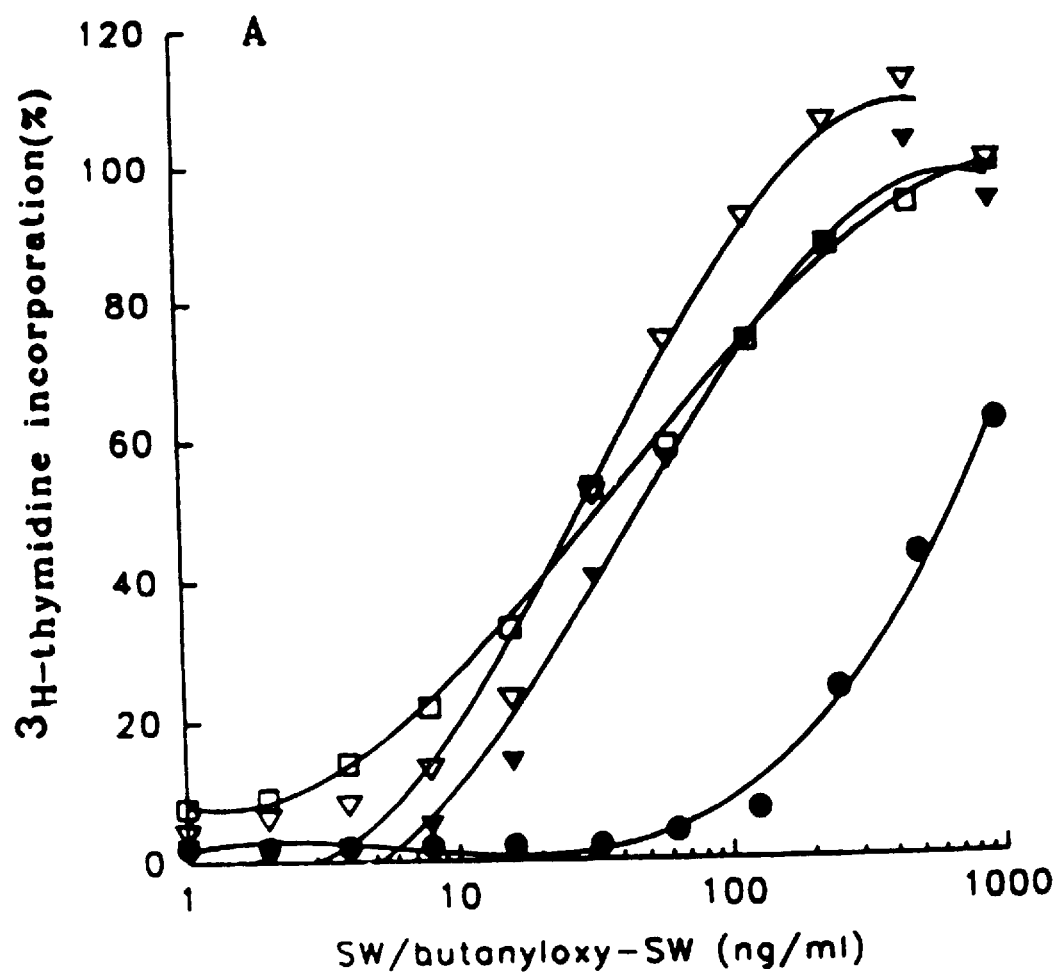
FIG. 6 is a graph showing L-PHA sensitivity of MDAY-D2 tumor cells in the presence of SW, (∇, □) and 2-butanoyloxy-SW (▼, ●); either without (open symbols), or in the presence of 0.5M diethyl p-nitrophenyl phosphate closed symbols)
Figure 7:
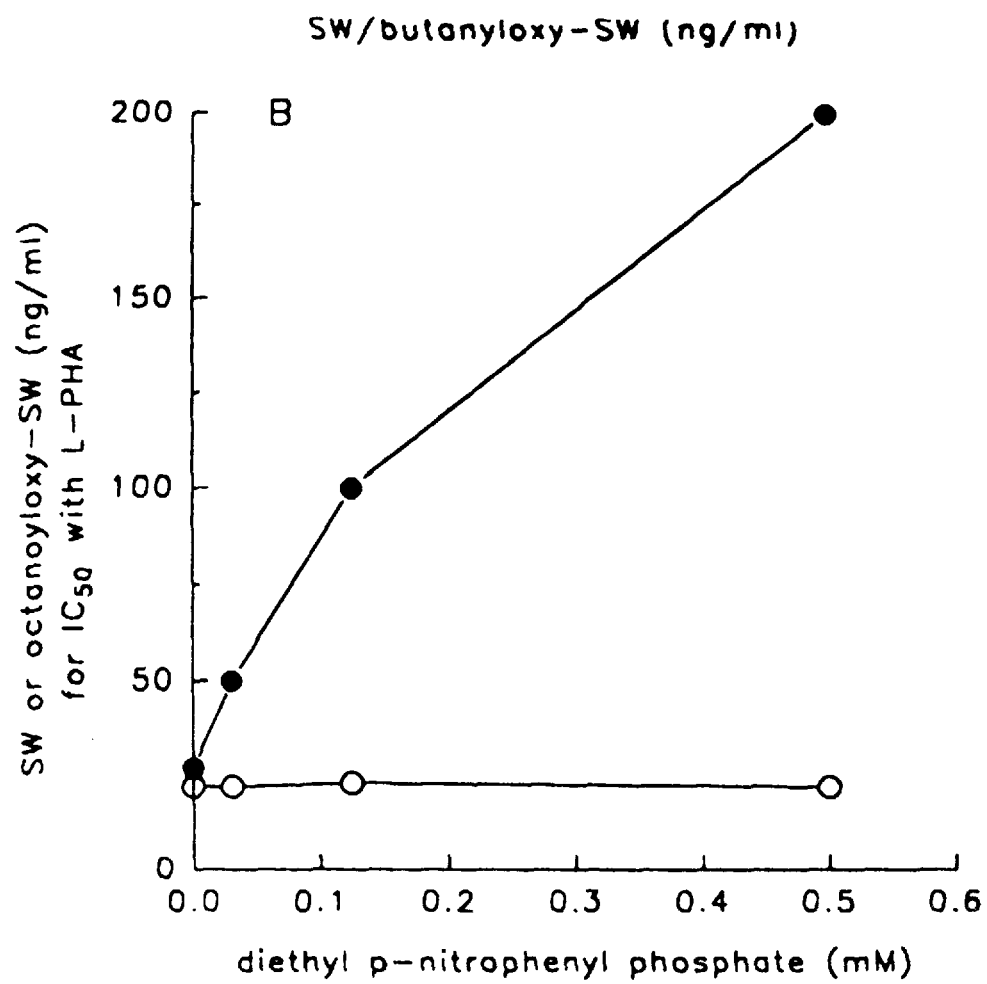
FIG. 7 is a graph showing SW (O); and 2-octanoyloxy-SW (●) concentrations required for 50% inhibition of L-PHA toxicity as a function of diethyl p-nitrophenyl phosphate concentration.

Although 2-p-nitrobenzoyloxy-SW, 2-octanoyloxy-SW and 2-butanoyloxy-SW showed a 300 fold greater $IC_{50}$ for α-mannosidase in vitro, the compounds had activities similar to that of SW for protection of MDAY-D2 tumor cells against L-PHA toxicity (Table 1). It is possible that either the analogues were much more efficient inhibitors of Golgi α-mannosidase than the Jack Bean and lysosomal enzymes, or more likely, that cellular esterases converted the analogues to SW inside the cells. To examine the latter possibility, the L-PHA toxicity assay was preformed in the presence of the esterase inhibitor diethyl p-nitrophenylphosphate. The $IC_{50}$ for inhibition of Golgi oligosaccharide processing by 2-butanoyloxy-SW was increased 10 fold by 0.5M diethyl p-nitrophenylphosphate (FIG. 6). Similar results were obtained for 2-octanoyloxy-SW, and the results in FIG. 7 show a titration for the effect of diethyl p-nitrophenylphosphate on $IC_{50}$ in the L-PHA toxicity assay.

SW ($IC_{50}$=0.2 μM) was compared with 2-toluoyloxy-SW ($IC_{50}$=3.4 μM) and 2-octanoyloxy-SW ($IC_{50}$ =0.23 μM) for inhibition of lung colonization by B16F10melanoma cells. Tumor cells were cultured in the presence of 20, 100 or 1000 ng/ml of drug for 48 hr, then washed in phosphate-buffered saline and injected intravenously into syngeneic mice. SW at 1000 ng/ml has been shown previously to inhibit organ colonization by B16F10melanoma cells by >90%, yet the drug does not reduce viability or clonigenicity of the tumor cells in vitro (Dennis J. W., Cancer Res., 46, 5131–5136, 1986 and Dennis et al., Cancer Inst., 81-1028–1033, 1989). The survival of mice 28 days after being injected with SW-treated or 2-octanoyloxy-SW treated tumor cells was significantly higher than mice injected with the same number of 2-toluoyloxy-SW treated or untreated B16F10 cells (Table 2). The anti-metastatic activity of the compounds correlated with their $IC_{50}$ for inhibition of L-PHA toxicity; that is SW~2-octanoyloxy-SW>2-toluoyloxy-SW.

To compare the myeloproliferative activity of the SW analogues in vivo, mice were injected intraperitoneally with the compound twice daily for 4 days, a regimen previously shown to be optimal for SW-induced BM proliferation (White et al., Cancer Commun. 3:83–91, 1991). BM cells were flushed from the femurs of the mice, and the total number of cells recovered was determined to be 2–3 fold greater for mice injected with SW or the analogues (Table 3). To determine whether the analogues of SW affected the number of pluripotent haematopoietic stem cells present in unfractionated BM, in vitro progenitor assays were performed. The CFU increased 2–3 fold in BM from SW-and analogue-treated mice compared to vesical treated mice. The stimulatory effect of the compounds was dose and time dependent. Dose curves were preformed for each compound (i.e., 5, 10, 20, and 40 μg/injection, data not shown) and the optimum for both BM cellularity and CFU was observed at 10 μg/injection, similar to that previously reported for SW (White et al., Cancer Commun. 3:83–91, 1991). Maximum stimulation was observed after 5–6 days of treatment. The response was not increased by prolonged administration of any of the analogs (data not shown).

In summary, carbonoyloxy substitutions at the 2 and 8 carbons of SW reduced inhibitor activity by 2–3 orders of magnitude for Jack Bean and MDAY-D2 tumor cell lysosomal α-mannosidases in vitro. However, 2-p-nitrobenzoyloxy-, 2-octanoyloxy-and 2-butanoyloxy-derivatives of SW retained full activity as inhibitors of Golgi oligosaccharide processing in viable MDAY-D2 tumor cells. Inhibition of oligosaccharide processing was reduced by the esterase inhibitor diethyl p-nitrophenylphosphate, suggesting that although 2-p-nitrobenzoyloxy-SW, 2-octanoyloxy-SW and 2-butanoyloxy-SW are relatively poor inhibitors of α-mannosidases in vitro, the compounds enter cells at a comparable rates to that of SW, and are converted to SW by cellular esterases. The more lipophylic esters, 2-benzoyloxy-SW, 2-toluoyloxy-SW, 8-palmitoyloxy-SW and 8-myristinoyloxy-SW showed $IC_{50}$ values at least 10 times higher for inhibition of Golgi oligosaccharide processing, probably due to less efficient entry of the compounds into tumor cells. The anti-metastatic activity of SW and two analogues were tested and shown to correlated with $IC_{50}$ for inhibition of Golgi oligosaccharide processing in cultured tumor cells. In vivo, SW and the analogues were administered intra-peritoneally to mice and found to have comparable activities as stimulators of bone marrow cell proliferation.

2-p-nitrobenzoyloxy-SW, 2-octanoyloxy-SW and 2-butanoyloxy-SW or similar analogues may be useful as prodrugs with 300 fold less activity until they are cleaved by esterases. Ideally, 2-or 8-substitutions to SW that are preferentially hydrolized in tumor cell and/or lymphoid cells would be expected to have improved pharmacologic properties and reduced side effects. Furthermore, carbonoyloxy-linked groups at the 2-or 8-position of SW which have anti-tumor or immune-stimulatory activity on their own may be designed to create even more potent prodrugs.

Example 2

Preparation of 1,4dideoxy-1,4-imino-D-lyxitol

Figure 8:
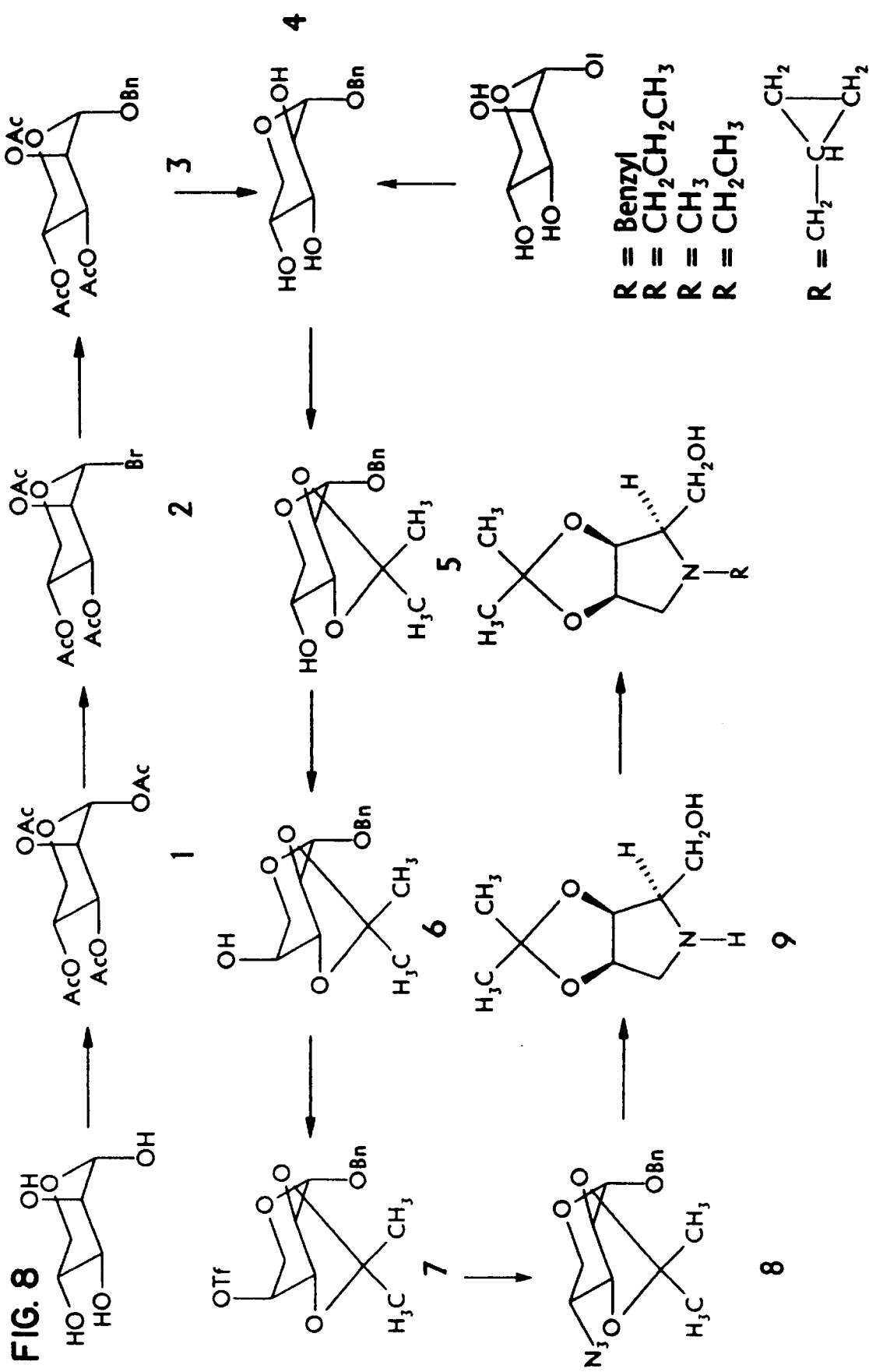
FIG. 8 is a schematic diagram of a process for preparing 1,4dideoxy-1,4imino-D-lyxitol.

A schematic diagram showing a method for preparing compounds of the formula I wherein $R^2$ is benzyl, $CH_2CH_2CH_3$, $CH_3$, $CH_2CH_3$, and cyclopropylmethyl is shown in FIG. 8 and described herein. The numbers in brackets in this example refer to the compounds shown in FIG. 8.

The following materials and methods were used in the investigations outlined in this example.

1H NMR and 13C NMR spectra were recorded at 300K in $CDCl_3$ with a Varian 500 MHz spectrometer using $Me_4Si$ as the internal reference for solutions in $CDCl_3$ and internal acetone for $D_2O$ solutions. Mass spectra were obtained on a AVG-Analytical ZAB-SE spectrometer. The samples were ionized by fast-atom bombardment (FAB). All reagents were purchased from Aldrich and solvents from BDH, the latter were dried by conventional methods.

(A) Preparation of 1,2,3,4-tetra-O-acetyl-D-lyxopyranose (1)

D-lyxose (10 g, 66.6 mmol) was dried by co-distillation with toluene (3×50 ml). It was further dried by vacuum pump for 3 hours. To the dried lyxose, anhydrous pyridine (50 ml) was added under argon and the mixture was cooled in an ice bath. After cooling for 15 minutes, acetic anhydride (50 ml) was added dropwise and the reaction mixture was left stirring at room temperature overnight. The reaction mixture was then concentrated under reduced pressure and the syrup was purified by filter technique on silica gel using hexane-ethyl acetate (1:1). Removal of the solvent gave a syrup (19.00 g, 89.6%) which was confirmed by Mass and NMR spectroscopy to be 1,2,3,4tetra-O-acetyl-D-lyxopyranose(1).

(B) Preparation of 2,3,4-tri-O-acetyl-α-lyxopyranosyl bromide (2)

Compound 1 (33.8 g, 106.2 mmol) was dissolved in $CH_2Cl_2$ (500 ml) under argon and cooled to −5° C. HBr gas was slowly bubbled into the solution with stirring for 20 minutes. This was gradually allowed to attain room temperature and stirred for 3 to 4 hours with continuing bubbling of HBr gas. Examination of the tlc suggested the formation of the bromo derivative with more than 90% yield. The solution was subjected to evaporation under vacuum. The traces of HBr and moisture were removed by co-distillation with toluene and vacuum desiccator drying over $P_2O_5$. The syrupy product was directly used for the next step.

(C) Preparation of Benzyl 2,3,4-tri-O-acetyl-α-D-lyxopyranoside (3)

A solution of compound 2 (21 g, 61.9 mmol) in acetonitrile (200 ml) and benzyl alcohol (9.6 ml, 92.3 mmol) was vigorously stirred with molecular sieves (4 Å, 25 g), mercury bromide (25 g, 69.4 mmol), mercury cyanide (18.2 g, 12.0 mmol) under argon for 18 hours. The organic layer was filtered through celite and diluted with dichloromethane (250 ml) which was washed with water, aq. $NaHCO_3$ and aq. NaCl and dried ($Na_2SO_4$). The solvent was filtered and then evaporated under reduced pressure. The syrupy residue was chromatographed on silica gel (filter technique) using 1.5:1 hexane-ethyl acetate to give 3 (21.8 g, 90.0%).

(D) Preparation of Benzyl α-D-lyxopyranoside (4)

A suspension of compound 3 (20 g) in dry methanol:dichloromethane (2:1, 400 ml) containing sodium methoxide in methanol (0.46 g. Na in 100 ml of methanol) was stirred at room temperature until starting product disappeared (tlc). The solution was then made neutral with mixed-bed resin (50 ml, BioRad AG501-X8), filtered and evaporated to dryness to give 4 (10.2 g, 76%).

(E) Direct Synthesis of Benzyl α-D-lyxopyranoside (4)

A mixture of D-lyxose (10 g, 66.6 mmol) and benzyl alcohol (50 ml) was cooled to −5° C. and hydrogen chloride was bubbled through it for 3 to 5 hours while monitoring the reaction on tlc (ethyl acetate-ethyl alcohol 7:1). To this reaction mixture diethyl ether (100 ml) was added with stirring and the mixture was allowed to stand at 5° C. for 12 hours. The crystals were filtered, washed with ether and air dried to give 4 (14.1 g, 88.1%).

(F) Preparation of Benzyl 2,3-O-isopropylidene α-D-lyxopyranoside (5)

To a solution of compound 4 (37 g, 176.0 mmol) in 800 ml of dry acetone were added 2,2-dimethoxypropane (39 ml, 318 mmol) and camphorsulphonic acid (1.5 g, 6.46 mmol). The solution was stirred under dry conditions for 2 to 3 hours and then was treated with $H_2O$ (200 ml) and aq. $NaHCO_3$ (300 ml). After stirring for 5 minutes, it was evaporated under vacuum. The syrupy product was extracted with $CH_2Cl_2$ (750 ml) and washed with $H_2O$. The organic layer was dried ($Na_2SO_4$), evaporated and submitted to the chromatogrphy (filter technique) with Hexane-ethyl acetate 2:1 and 1:1) as the eluant to yield 5 (33.0 g, 74.9%).

(G) Benzyl 2,3-isopropylidene α-L-ribopyranoside (6)

To a stirring mixture of 5 (33.0 g, 131.8 mmol), molecular sieves (3 Å, 66 g), anhydrous potassium carbonate (48 g, 347.3 mmol) in benzene (3000 ml) and pyridinium chlorochromate (64 g, 296.9 mmol) were carefully added. The reaction mixture was refluxed under argon for 20 minutes and then at room temperature for 30 minutes. The solution was filtered through a long bed of silica and celite. The funnel like column was then eluted with hexane-ethyl acetate (1:1) to give only the oxidized compound. The solvent was evaporated and the syrup was dissolved in a mixture of MeOH (2000 ml), CH$_2$Cl$_2$ (570 ml) and EtOH (280 ml). The solution was then treated with a slow addition of NaBH$_4$ (40 g). The reaction mixture was left stirring overnight. It was concentrated and purified directly on silica column (filter technique) with hexane-ethyl acetate (1:1) to give 6 (31 g, 93.9%).

(H) Preparation of Benzyl 2,3 -isopropylidene4-O-trifluoromethyl-sulfonyl-α-D-lyxopyranoside (7)

To a stirred solution of trifluoromethanesulfonic anhydride (40 ml, 237.7 mmol) in CH$_2$Cl$_2$ (150 ml) at −15° C. were added dropwise a solution of pyridine (50 ml) in CH$_2$Cl$_2$ (100 ml) followed by a chilled solution of 6 (31 g, 123.8 mmol) in CH$_2$Cl$_2$ (100 ml). Stirring was continued at −15° C. for 30 minutes, after which a single major spot was seen on tlc (hexane-ethyl acetate, 2:1). The mixture was shaken with an equal volume of iced water and the mixture was extracted with CH$_2$Cl$_2$. The combined organic phases were quickly washed with dilute aq. NaHCO$_3$ solution, dried (Na$_2$SO$_4$) and evaporated and co-distilled with toluene to give 7 which was immediately consumed for the next step.

(I) Preparation of Benzyl 4-azido-4-deoxy-2,3-isopropyhdene-α-D-lyxopyranoside (8)

The syrupy compound 7 and NaN$_3$ (40 g, 692.3 mmol) in N,N-dimethylformamide (300 ml) were stirred and heated at 100° C. under argon for 24 hours. The reaction mixture was cooled and diluted with CH$_2$Cl$_2$ (800 ml). The organic phase was washed with water several times and separated, dried (Na$_2$SO$_4$) and evaporated to a yellowish solid. The product was purified on silica gel (filter technique) using hexane and hexane-ethyl acetate (2:1) as eluant to give 8 (25 g, 74.0%).

(J) Preparation of 1,4-dideoxy-1,4-imino-2,3-O-isopropylidene-D-lyxitol (9)

To a round bottom flask containing palladium hydroxide on carbon (20% Pd, 8.33 g) in ethyl alcohol (400 ml), compound 8 (25 g, 81.9 mmol) dissolved in ethyl alcohol (266 ml) was slowly added. The reaction mixture was stirred under argon for few minutes. To this stirred solution, cyclohexene (416 ml) was added and the reaction mixture was refluxed under argon for 2 to 3 hours. After cooling, the catalyst was filtered off and washed exhaustively with methanol. The filtrate was concentrated and purified on silica gel (filter technique) using first ethyl acetate-MeOH (6:1) and then (1:1) to give 9 (5.4 g, 38.1%).

(K) Preparation of N-propyl-1,4-dideoxy-1,4-imino-2,3-O-isopropylidene-D-lyxitol (10)

A mixture of mono-ol 9 (100 mg, 0.577 mmol), ethyl alcohol (10 ml), palladium black (100 mg) and propanal (1 ml) was shaken in a Parr hydrogenating bottle under an atmosphere of hydrogen (2.4 atmos. pressure) for 24 hours. Filtration followed by removal of solvent gave an oily product which was purified by flash chromatography using ethyl acetate-MeOH (6:1.5) to give 10 (77 mg, 62%). Similarly N-R-1,4-dideoxy-1,4-imino-2,3-O-isopropylidene-D-lyxitol was prepared where R=methyl, ethyl, and cyclopropylmethyl.

(L) Preparation of N-butyl-1,4-dideoxy-1,4-imino-2,3-O-isopropylidene-lyxitol (11)

A mixture of 9 (52 mg, 0.30 mmol), ethyl alcohol (8 ml), palladium hydroxide on carbon (20% Pd, 45 mg), butanal (1 ml) and cyclohexene (4 ml) was refluxed with stirring under argon for 20 hours. The catalyst was filtered off and the solvent was removed to give an oily residue which was purified by flash chromatography (ethyl acetate-MeOH, 6:1) to give 11 (26 mg, 38.0%).

(M) Preparation of N-benzyl-1,4-dideoxy -1,4-imino-2,3 -O-isopropylidene-D-lyxitol (12).

Compound 9 (248 mg, 1.43 mmol) was stirred with benzyl bromide (0.25 ml) in CH$_2$Cl$_2$ (20 ml) containing aq. NaHCO$_3$ (10%, 5 ml) at 4° C. for 28 hours. Further addition of benzyl bromide (0.2 ml) was made and the mixture was left stirring at room temperature for 4 hours. The organic layer was separated, concentrated and purified by flash chromatography using hexane-ethyl acetate (1:3) as an eluant to produce 12 (350 mg, 87.5%).

Example 3

The activities of selected compounds of the invention in the LPH-A toxicity assay described herein are shown in Table 4.

Example 4

The assay for rat liver Golgi α-mannosidase II contained 5 mM para-nitrophenylα-mannose, 40 mM sodium acetate pH 5.6, plus serially diluted test compouunds and mannosidase enzyme in a total volume of 50 ul, in 96 well plates. Plates were incubated 45 min at 37° C., then the reaction was stopped with 50 μl of 0.5M sodium carbonate. The absorbance of reaction products was read at 405 nM. The lysosomal mannosidase was done in the same procedure but with 40 mM sodium acetate buffer pH 5.0. The results are shown in Table 5 and the compounds tested are shown in Table 6. The numbers in the table are IC$_{50}$ values in μM for inhibition of mannosidase activity. The compound designated CD002 is favourable to Mannosidase II and is therefore a preferred therapeutic agent.

From the foregoing, it will be appreciated that, although specific embodiments of the invention have been described herein for purposes of illustration, various modifications may be made without deviating from the spirit and scope of the invention Accordingly, the invention is not limited except as by the appended claims.

TABLE 1

Inhibition of Oligosaccharide processing and α-mannosidases by SW-analogues.

| SW derivative of | IC$_{50}$ for Inhibition L-PHA Toxicity (uM) | IC$_{50}$ for inhibition of J.B. α-mannosidase (uM) | IC$_{50}$ for inhibition of MDAY-D2 α-mannosidase (uM) |
|---|---|---|---|
| SW | 0.20 | 0.4 | 0.5 |
| 2-benzoyloxy-SW | 1.80 | 350.0 | 720.0 |
| 2-toluoyloxy-SW | 3.40 | 350.0 | 69.0 |
| 2-p-nitrobenzoyloxy-SW | 0.23 | 123.0 | 35.0 |

TABLE 1-continued

Inhibition of Oligosaccharide processing and α-mannosidases by SW-analogues.

| SW derivative of | IC$_{50}$ for Inhibition L-PHA Toxicity (uM) | IC$_{50}$ for inhibition of J.B. α-mannosidase (uM) | IC$_{50}$ for inhibition of MDAY-D2 α-mannosidase (uM) |
|---|---|---|---|
| 2-octanoyloxy-SW | 0.23 | 123.0 | 35.0 |
| 2-butanoyloxy-SW | 0.23 | 123.0 | 35.0 |
| 8-palmitoyloxy-SW | >2.50 | 240.0 | 500.0 |
| 8-myristinoyloxy-SW | >2.50 | >500.0 | >500.0 |
| 6,7-dihydroxy-SW | >5.00 | 50.0 | 10.0 |

The IC for inhibition of L-PHA toxicity was determined using MDAY-D2 tumor cells as described in Materials and Methods; also see FIG. 4. The IC$_{50}$ for inhibition of Jack Bean (J.B.) and MDAY-D2 lysosomal α-mannosidases were determined as described in Methods section; see FIG. 5.

TABLE 2

Lung colonization by B16F10 melanoma cells cultured in the presence of SW, 2-toluoyloxy-SW, and 2-octanoyloxy-SW.

| Treatment | Dose (ug/ml) | Survivors at day 28 | lung colonies (mean ± range) |
|---|---|---|---|
| None | — | 0/8 | >100 |
| SW | 1.0 (5.8 uM) | 4/5 | 3 (0–4) |
|  | 0.1 | 4/5 | 5 (2–10) |
|  | 0.02 | 2/5 | 23 (15–31) |
| 2-octanoyloxy-SW | 1.0 (3.3 uM) | 2/5 | 1 (0–2) |
|  | 0.1 | 3/5 | 13 (8–20) |
|  | 0.02 | 3/5 | 9 (5–17) |
| 2-toluoyloxy-SW | 1.0 (3.4 uM) | 0/5 | >100 |
|  | 0.1 | 0/5 | >100 |

B16F10 melanoma cells were injected into the lateral tail vein of C57B1/6 mice at 105 cells/mouse. Prior to the injection, tumor cells had been cultured for 48 hr eiTher untreated, or treated with the indicated concentration of SW, or 2-octanoyloxy-SW, or 2-toluoyloxy-SW. The experiment was terminated on day 28 and lung colonies in the mice were counted.

TABLE 3

Stimulation of bone marrow cell proliferation in vivo by SW and SW-analogues.

| Treatment | BM cellularity (cells × 10$^7$) | CFU (colonies/10$^7$ cells) |
|---|---|---|
| PBS | 1.46 ± 0.08 | 145 ± 4 |
| SW | 4.50 ± 0.42 | 540 ± 34 |
| 2-benzoyloxy-SW | 5.77 ± 0.00 | 421 ± 44 |
| 2-toluoyloxy-SW | 3.40 ± 0.25 | 384 ± 25 |
| 2-p-nitrobenzoyloxy-SW | 3.60 ± 0.42 | 380 ± 7 |
| 2-octanoyloxy-SW | 3.88 ± 4.43 | 482 ± 22 |
| 2-butanoyloxy-SW | 3.80 ± 0.91 | 545 ± 59 |
| 8-palmitoyloxy-SW | 5.10 ± 0.57 | 553 ± 32 |
| 8-myristinoyloxy-SW | 4.80 ± 0.24 | 226 ± 6 |
| 6,7-dihydroxy-SW | 5.20 ± 0.03 | 538 ± 5 |

Mice were given twice daily intraperitoneal injections of PBS, SW or the analogues at 10 ug/injection. After four days of injections, BM cells were flushed from the femurs and tibias and counted. CFUs growing in soft agar consisting of at least 40 cells were enumerated. The results are the mean +/−S.E. of 4 experiments.

TABLE 4

Inhibition of oligosaccharide processing in MDAY-D2 mouse lymphoma cells

| Compound | Toxicity (mM)+ | IC$_{50}$ (mM)* |  |
|---|---|---|---|
| GD0003 | none at 5 mM | 0.312 | N-methyl-DIL++ |
| GD0004 | >2.5 mM | 0.625 | N-butyl-DIL |
| GD0005 | none at 5 mM | 0.312 | N-ethyl-DIL |
| GD0006 | >2.5 mM | 0.156 | N-propyl-DIL |
| GD0008 | >2.5 | 0.040 | N-cyclo-propyl-methyl-DIL |

*IC$_{50}$ for protection of cells from toxicity of L-PHA lectin.
+cellular toxicity observed with compound alone.
++Where DIL is 1,4-dideoxy-1,4-imino-D-lyxitol

TABLE 5

| | IC$_{50}$ Values | | |
|---|---|---|---|
| | ManII (uM) | lyso (uM) | Ratio |
| SW | 0.10 | 0.082 | 0.82 |
| GD002 | 19.0 | 217 | 11.42 |
| GD003 | 26.3 | 13.6 | 0.517 |
| GD004 | 50.9 | 25.5 | 0.50 |
| GD005 | 33.9 | 14.3 | 0.42 |
| GD006 | 22.1 | 19.2 | 0.87 |
| GD008 | 8.3 | 4.9 | 0.59 |
| GD013 | 114 | 193 | 1.69 |
| GD014 | 140 | 157 | 1.12 |

TABLE 6

| Compound | Structural Formula |
|---|---|
| GD002 | HO,,,,,⟨pyrrolidine ring⟩,,,,OH; ring N–CH$_2$–Ph substituent; CH$_2$OH group |
| GD003 | HO,,,,,⟨pyrrolidine ring⟩,,,,OH; ring N–CH$_3$ substituent; CH$_2$OH group |

TABLE 6-continued

| Compound | Structural Formula |
|---|---|
| GD004 | (structure) |
| GD005 | (structure) |
| GD006 | (structure) |
| GD008 | (structure) |
| GD0013 | (structure) |
| GD0014 | (structure) |

We claim:
1. A compound of the formula I

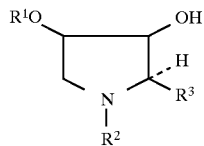

wherein
$R^1$ is hydrogen or p-nitrobenzoyloxy, -octanoyloxy or -butanoyloxy;
$R^2$ is hydrogen, ($C_1$–$C_5$)-alkyl, methyl cyclopropane, methyl cyclohexane, tertiary butyl or benzyl;
$R^3$ is —COOR$^4$ wherein $R^4$ is p-nitrobenzyl, octyl, or butyl;
—(CHOR$^1$)COOR$^4$ wherein $R^4$ is as defined above;
—CHR$^2$OR$^1$ wherein $R^1$ and $R^2$ are as defined above;
—(CHOR$^1$)(CHR$^2$OR$^1$) wherein $R^1$ and $R^2$ are as defined above;
—(CHOR$^1$)(CH$_2$R$^6$) wherein $R^1$ is as defined above and $R^6$ is a halogen preferably fluorine, chlorine, iodine or bromine; —CH$_2$R$^6$ wherein $R^6$ is as defined above; —CH$_2$O—CO—R$^4$ wherein $R^4$ is as defined above; or —CHR$^9$OH wherein $R^9$ is (C1–C5)-alkyl; with the proviso that when $R^1$ is hydrogen and $R_3$ is —(CHOH)(CH$_2$OH), $R^2$ cannot be methyl, n-butyl or benzyl and that when $R^1$ and $R^2$ are hydrogen, $R_3$ cannot be —CH$_2$OH, —(CHOH)CH$_3$, —(CHOH)(CH$_2$F) or —(CHOH)(CH$_2$OH).

2. The process for the preparation of a compound of the formula I as defined in claim 1 which comprises (i) N-alkylating 1,4-dideoxy-1,4-imino-2,3-O-isopropylidene-α-D-lyxitol which is protected at the C5 position or 1,4-dideoxy-1,4-imino-2,3-O-isopropylidene-α-D-mannitol which is protected at the C5 and C6 position, under suitable conditions with a compound of the formula R$^5$CHO wherein $R^5$ is ($C_1$–$C_5$)-alkyl, tertiary butyl or benzyl, cyclopropyl, and cyclohexyl, when a compound of the formula I is required wherein $R^2$ is ($C_1$–$C_5$)-alkyl, methyl cyclopropane, methyl cyclohexane, tertiary butyl or benzyl;

(ii) reacting 1,4-dideoxy-1,4-imino-2,3-O-isopropylidene-α-D-lyxitol or 1,4-dideoxy-1,4-imino-2,3-O-isopropylidene-α-D-mannitol with a compound of the formula R$^6$—CO—R$^4$ wherein $R^6$ is a halogen preferably fluorine, chlorine, iodine, and bromine and $R^4$ is p-nitrobenzyl, octanyl or butyl under alkaline conditions, when a compound of the formula I is required wherein $R^3$ is CH$_2$O—CO—R$^4$ wherein $R^4$ is as defined above or a compound of the formula I is required wherein $R^3$ is (CHOH)CH$_2$OCOR$^4$;

(iii) reacting 1,4-dideoxy-1,4-imino-2,3-O-isopropylidene-α-D-lyxitol or 1,4-dideoxy-1,4-imino-2,3-O-isopropylidene-α-D-mannitol with triphenyl phosphine and C(R$^6$)$_4$ wherein $R^6$ is halogen preferably fluorine, chlorine, iodine or bromine, when a compound of the formula I is required wherein $R^3$ is CH$_2$R$^6$ wherein $R^6$ is as defined above or a compound of the formula I is required wherein $R^3$ is (CHOH)CH$_2$R$^6$ wherein $R^1$ and $R^6$ are as defined above, and esterifying the 6-deoxy-6-halo-mannitol derivative using the methods given when a compound of the formula I is required wherein $R^3$ is (CHOR$^1$)CH$_2$R$^6$ wherein $R^1$ and $R^6$ are as defined above;

(iv) preparing a 2,3-benzyl derivative from 1,4-dideoxy-1,4-imino-2,3-O-isopropylidene-α-D-lyxitol or 1,4-dideoxy-1,4-imino-2,3-O-isopropylidene-α-D-mannitol after removing the isopropylidene and then oxidizing the derivative to prepare a compound of the formula I wherein $R^3$ is —COOH, and reacting with a compound of the formula R$^2$OH, or a compound of the formula I is required wherein $R^3$ is (CHOH)CH$_2$R$^6$ wherein $R^1$ and $R^6$ are as defined above, and esterifying the 6-deoxy-6-halo-mannitol derivative using the methods given when a compound of the formula I is required wherein $R^3$ is (CHOR$^1$)CH$_2$R$^6$ wherein $R^1$ and $R^6$ are as defined above, to produce compounds of the formula I wherein $R^3$ is —COOR$^2$ or —(CHOH)COOR$^2$ and $R^2$ is as defined above;

(v) protecting the C5 position of 1,4-dideoxy-1,4-imino-2,3-O-isopropylidene-α-D-lyxitol or the C5 and C6 positions of 1,4-dideoxy-1,4-imino-2,3-O- isopropylidene-α-D-mannitol removing the isopropylidene, and then selectively esterifying by reacting with a compound of the formula

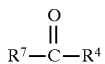

wherein $R^7$ is a benzotriazol or a halogen preferably fluorine, chlorine, iodine or bromine and $R^4$ is p-nitrobenzyl, octyl or butyl when a compound of the formula I is required wherein $R^1$ is p-nitrobenzoyloxy, -octanoyloxy or -butanoyloxy; or (vi) oxidizing 1,4-dideoxy-1,4-imino-2,3-O-isopropylidene-α-D-lyxitol with an oxidizing agent or selectively oxidizing the primary alcohol in 1,4-dideoxy-1,4-imino-2,3-O-isopropylidene-α-D-mannitol and then reacting either with a compound of the formula $R^9$:Mg:$R^6$ wherein $R^9$ is $(C_1$–$C_5)$-alkyl, and $R^6$ is halogen preferably fluorine, chlorine, iodine or bromine when a compound of the formula I is required in which R3 is $CHR^9OH$ and $R^9$ is (C1–C5) -alkyl or when a compound of the formula I is required wherein $R^3$ is —(CHOH)$CHR^9OH$ wherein $R^9$ is (C1–C5)-alkyl; and optionally when a compound of the formula I is required wherein $R^2$ is other than hydrogen, N-alkylating using the methods described above in (i); and/or where compounds of the formula I are required wherein $R^1$ is other than hydrogen esterifying using the methods set out in (v).

3. A compound of the formula IV

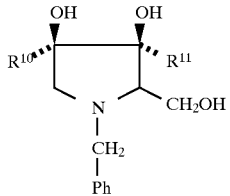

wherein $R^{10}$ and $R^{11}$ are the same or different and represent hydrogen, hydroxyl, halo, amino, alkoxy, alkyl or aryl, and Ph represents phenyl.

4. A compound of the formula IV as claimed in claim 3 wherein $R^{10}$ and $R^{11}$ are hydrogen.

5. A method for identifying a substance which can be used as prodrug which inhibits N-linked oligosaccharide processing comprising growing transformed cells in the presence of L-PHA, the substance and an esterase inhibitor; measuring the amount of proliferation of the cells; and comparing the amount of proliferation of the cells with the amount of proliferation observed for the cells grown in the presence of L-PHA and the substance alone.

6. A method of treating neoplasia, microbial infections and antiproliferative conditions comprising administering a compound of the formula II as a prodrug

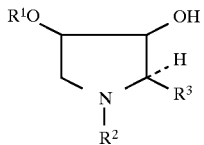

wherein
$R^1$ is hydrogen or p-nitrobenzoyloxy, -octanoyloxy or-butanoyloxy;
$R^2$ is a bond, hydrogen, $(C_1$–$C_5)$-alkyl, methyl cyclopropane, methyl cyclohexane, tertiary butyl or benzyl;

$R_3$ is —$COOR^4$ wherein $R^4$ is p-nitrobenzyl, octyl, or butyl; as defined above; —(CHOR$^1$)COOR$^4$ wherein $R^4$ is as defined above; —CHR$^2$OR$^1$ wherein $R^1$ and $R^2$ are as defined above;
—(CHOR$^1$)(CHR$^2$OR$^1$) wherein $R^1$ and $R^2$ are as defined above; —CH$_2$O—CO—R$^4$ wherein $R^4$ is as defined above; —(CHOR$^1$)(CH$_2$R$^6$) wherein $R^1$ is as defined above and $R^6$ is a halogen preferably fluorine, chlorine, iodine or bromine; —CH$_2$R$^6$ wherein $R^6$ is as defined above; or when $R^2$ is a bond, $R_3$ is —CHR$^8$CH$_2$CH$_2$CH$_2$— which together with N forms a ring wherein $R^8$ is p-nitrobenzoyloxy, -octanoyloxy or -butanoyloxy, with the proviso that when $R^1$ is hydrogen and $R^3$ is —(CHOH)(CH$_2$OH), $R^2$ cannot be methyl, n-butyl or benzyl and that when $R^1$ and $R^2$ are hydrogen, $R^3$ cannot be —CH$_2$OH, —(CHOH)CH$_3$, —(CHOH)(CH$_2$F) or —(CHOH)(CH$_2$OH).

7. The pharmaceutical composition comprising a compound as claimed in claim 1, 3 or 4 and a pharmaceutically acceptable carrier, diluent or excipient.

8. The compound of the formula I as claimed in claim 1 wherein $R^2$ is —CH$_2$CH$_3$ and $R^3$ is —CH(CH$_3$)OH.

9. The compound of the formula I as claimed in claim 1 wherein $R^2$ is —CH$_2$CH$_2$CH$_3$ and $R^3$ is —CH$_2$OH.

10. The compound of the formula I as claimed in claim 1 wherein $R^2$ is —CH$_3$ and $R^3$ is —CH(CH$_2$CH$_3$)OH.

11. The compound of the formula I as claimed in claim 1 wherein $R^2$ is —H and $R^3$ is —CH(CH$_2$CH$_2$CH$_3$)OH.

12. The compound of the formula I as claimed in claim 1 wherein $R^1$ is p-nitrobenzoyloxy, -octanoyloxy or -butanoyloxy, $R^2$ is hydrogen, and $R^3$ is —(CHOH)CH$_2$OH.

13. The compound of the formula I as claimed in claim 1 wherein $R^1$ and $R^2$ are hydrogen, and $R^3$ is —(CHOH)CH$_2$OR$^1$ wherein $R^1$ is p-nitrobenzoyloxy, -octanoyloxy or -butanoyloxy.

14. The compound of the formula I as claimed in claim 1 wherein $R^1$ is p-nitrobenzoyloxy, -octanoyloxy or -butanoyloxy, $R^2$ is hydrogen, and $R^3$ is —(CHOH)CH$_2$OR$^1$ wherein $R^1$ is p-nitrobenzoyloxy, -octanoyloxy or -butanoyloxy.

15. The compound of the formula I as claimed in claim 1 wherein $R^1$ and $R^2$ are hydrogen, $R^3$ is —COOR$^4$ wherein $R^4$ is p-nitrobenzyl, octyl or butyl.

16. The compound of the formula I as claimed in claim 1 wherein $R^1$ is p-nitrobenzoyloxy, -octanoyloxy or -butanoyloxy, $R^2$ is —CH$_2$CH$_2$CH$_3$, and $R^3$ is —CH$_2$OH.

17. The compound of the formula I as claimed in claim 1 wherein $R^1$ is hydrogen, $R^2$ is —CH$_2$CH$_2$CH$_3$, and $R^3$ is —CH$_2$OR$^1$ wherein $R^1$ is p-nitrobenzoyloxy, -octanoyloxy or -butanoyloxy.

18. The compound of the formula I as claimed in claim 1 wherein $R^1$ is hydrogen, $R^2$ is —CH$_2$CH$_3$, and $R^3$ is —CH(CH$_3$)OR$^1$ wherein $R^1$ is p-nitrobenzoyloxy, -octanoyloxy or -butanoyloxy.

19. The compound of the formula I as claimed in claim 1 wherein $R^1$ is hydrogen, $R^2$ is —CH$_3$, and $R^3$ is —CH(CH$_2$CH$_3$)OR$^1$ wherein $R^1$ is p-nitrobenzoyloxy, -octanoyloxy or -butanoyloxy.

20. The compound of the formula I as claimed in claim 1 wherein $R^1$ is hydrogen, $R^2$ is hydrogen, and $R^3$ is —CH(CH$_2$CH$_2$CH$_3$)OR$^1$ wherein $R^1$ is p-nitrobenzoyloxy, -octanoyloxy or -butanoyloxy.

21. The compound of the formula I as claimed in claim 1 wherein $R^1$ is p-nitrobenzoyloxy, -octanoyloxy or butanoyloxy, $R^2$ is —CH$_3$, and $R^3$ is —CH(CH$_2$CH$_3$)OR$^1$ wherein $R^1$ is p-nitrobenzoyloxy, -octanoyloxy or -butanoyloxy.

22. The compound of the formula I as claimed in claim 1 wherein $R^1$ is p-nitrobenzoyloxy, -octanoyloxy or butanoyloxy, $R^2$ is hydrogen, and $R^3$ is —CH(CH$_2$CH$_2$CH$_3$) OR$^1$ wherein $R^1$ is p-nitrobenzoyloxy, -octanoyloxy or -butanoyloxy.

23. The compound of the formula I as claimed in claim 1 wherein $R^1$ is hydrogen, $R^2$ is benzyl and $R^3$ is —CH$_2$OH.

24. The compound of the formula I as claimed in claim 1 wherein $R^1$ is hydrogen, $R^2$ is —CH$_3$ and $R^3$ is —CH$_2$OH.

25. The compound of the formula I as claimed in claim 1 wherein $R^1$ is hydrogen, $R^2$ is —CH$_2$CH$_2$CH$_2$CH$_3$ and $R^3$ is —CH$_2$OH.

26. The compound of the formula I as claimed in claim 1 wherein $R^1$ is hydrogen, $R^2$ is —CH$_2$CH$_3$ and $R^3$ is —CH$_2$OH.

27. The compound of the formula I as claimed in claim 1 wherein $R^1$ is hydrogen, $R^2$ is methyl cyclopropane and $R^3$ is —CH$_2$OH.

28. The compound of the formula I as claimed in claim 1 wherein $R^1$ is hydrogen, $R^2$ is methyl cyclopropane and $R^3$ is —CH$_2$(CH$_3$)OH.

29. The compound of the formula I as claimed in claim 1 wherein $R^1$ is hydrogen, $R^2$ is methyl cyclohexane and $R^3$ is —CH$_2$(CH$_3$)OH.

30. The compound of the formula I as claimed in claim 1 which is in the form of a salt.

31. The pharmaceutical composition comprising a compound as claimed in any one of claims 8 to 30, and a pharmaceutically acceptable carrier, diluent, or excipient.

* * * * *